United States Patent
Pacanowsky et al.

(10) Patent No.: US 8,480,759 B2
(45) Date of Patent: Jul. 9, 2013

(54) ADJUSTABLE PROSTHESIS

(75) Inventors: Alex Pacanowsky, Salt Lake City, UT (US); Brian Glaister, Seattle, WA (US); Jason Schoen, Seattle, WA (US); Kathleen Mulholland, Seattle, WA (US)

(73) Assignee: Cadence Biomedical, Inc., Seattle, WA (US)

( * ) Notice: Subject to any disclaimer, the term of this patent is extended or adjusted under 35 U.S.C. 154(b) by 265 days.

(21) Appl. No.: 12/769,387

(22) Filed: Apr. 28, 2010

(65) Prior Publication Data

US 2010/0274364 A1    Oct. 28, 2010

Related U.S. Application Data

(60) Provisional application No. 61/173,205, filed on Apr. 28, 2009, provisional application No. 61/173,208, filed on Apr. 28, 2009, provisional application No. 61/242,675, filed on Sep. 15, 2009, provisional application No. 61/244,449, filed on Sep. 22, 2009.

(51) Int. Cl.
    *A61F 2/80*    (2006.01)

(52) U.S. Cl.
    USPC .......................................................... 623/36

(58) Field of Classification Search
    USPC .......................................................... 623/36
    See application file for complete search history.

(56) References Cited

U.S. PATENT DOCUMENTS

| | | | |
|---|---|---|---|
| 1,216,367 A | 2/1917 | Rowley | |
| 1,868,303 A | 7/1932 | Balch et al. | |
| 2,010,482 A | 8/1935 | Cobb ................................... 3/1 |
| 2,025,835 A | 12/1935 | Trautman | |
| 2,533,404 A * | 12/1950 | Sharp et al. ...................... 623/36 |
| 2,652,570 A | 9/1953 | Sargeson | |
| 4,635,626 A * | 1/1987 | Lerman ........................... 602/61 |
| 5,621,985 A | 4/1997 | Frost ................................. 36/89 |
| 5,658,242 A | 8/1997 | McKay et al. ................... 602/16 |
| 5,662,693 A | 9/1997 | Johnson et al. ................. 607/49 |
| 5,728,169 A * | 3/1998 | Norvell ........................... 623/36 |
| 5,888,231 A * | 3/1999 | Sandvig et al. ................. 623/36 |
| 5,899,869 A | 5/1999 | Barrack, Jr. et al. ........... 602/16 |
| 5,961,476 A | 10/1999 | Betto et al. ..................... 602/16 |
| 6,544,292 B1 * | 4/2003 | Laghi .............................. 623/36 |
| 6,689,074 B2 | 2/2004 | Seto et al. ........................ 601/5 |
| 6,702,858 B2 | 3/2004 | Christensen | |
| 6,923,834 B2 | 8/2005 | Karason | |

(Continued)

FOREIGN PATENT DOCUMENTS

| | | |
|---|---|---|
| EP | 0363654 B1 | 4/1990 |
| GB | 2 278 041 A | 11/1994 |
| SU | 1437046 A1 | 11/1988 |

*Primary Examiner* — Bruce E Snow
*Assistant Examiner* — Melissa Hoban
(74) *Attorney, Agent, or Firm* — Perkins Coie LLP

(57) ABSTRACT

A prosthesis system includes a reconfigurable socket. The socket changes configurations to adjust the socket fit. The socket includes a socket main body with a window and a panel positioned in the window. The panel and the socket main body cooperate to define a cavity for receiving a residual limb. A lacing system is coupled to both the socket main body and the panel and moves the panel with respect to the socket main body to adjust a volume of the cavity. A tensioning mechanism holds the lacing system to position the adjustment panel. The prosthesis system also allows for the escape of moisture from within the cavity.

24 Claims, 20 Drawing Sheets

U.S. PATENT DOCUMENTS

| | | |
|---|---|---|
| 6,991,657 B1 | 1/2006 | Price, Jr. |
| 7,427,297 B2 | 9/2008 | Patterson et al. |
| 7,488,349 B2 | 2/2009 | Einarsson |
| 7,549,969 B2 | 6/2009 | van den Bogert ............... 602/16 |
| 7,670,386 B2 | 3/2010 | Ezenwa |
| 2001/0016781 A1* | 8/2001 | Caspers .......................... 623/34 |
| 2002/0094919 A1 | 7/2002 | Rennex et al. ................ 482/124 |
| 2003/0078674 A1 | 4/2003 | Phillips |
| 2003/0144620 A1 | 7/2003 | Sieller et al. ...................... 602/5 |
| 2004/0167447 A1* | 8/2004 | Johnson, III ...................... 602/5 |
| 2005/0149202 A1* | 7/2005 | Schaffer et al. ................. 623/36 |
| 2005/0267599 A1* | 12/2005 | Bjarnason ....................... 623/36 |
| 2007/0055383 A1 | 3/2007 | King |
| 2007/0225824 A1 | 9/2007 | Einarsson ....................... 623/36 |
| 2008/0147204 A1 | 6/2008 | Ezenwa .......................... 623/33 |
| 2008/0161939 A1 | 7/2008 | Perkins .......................... 623/36 |
| 2008/0221706 A1* | 9/2008 | Scussel et al. .................. 623/32 |

\* cited by examiner

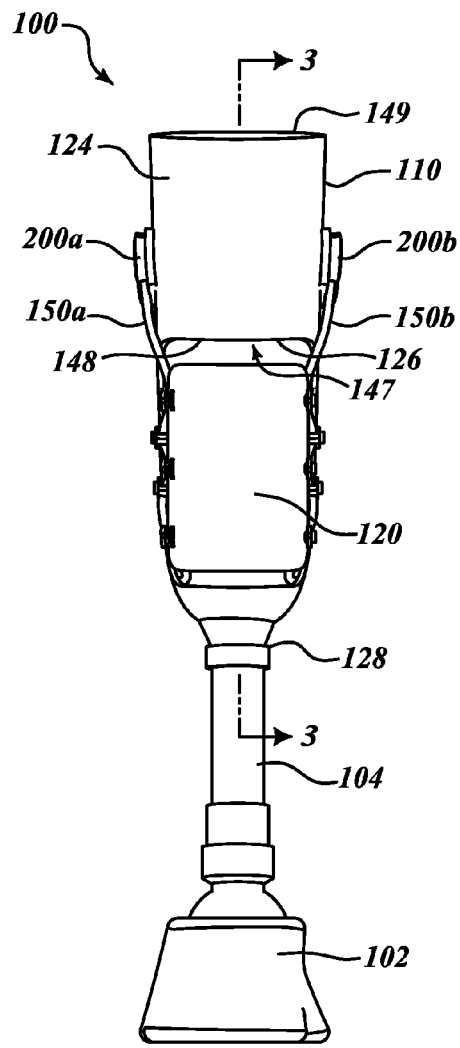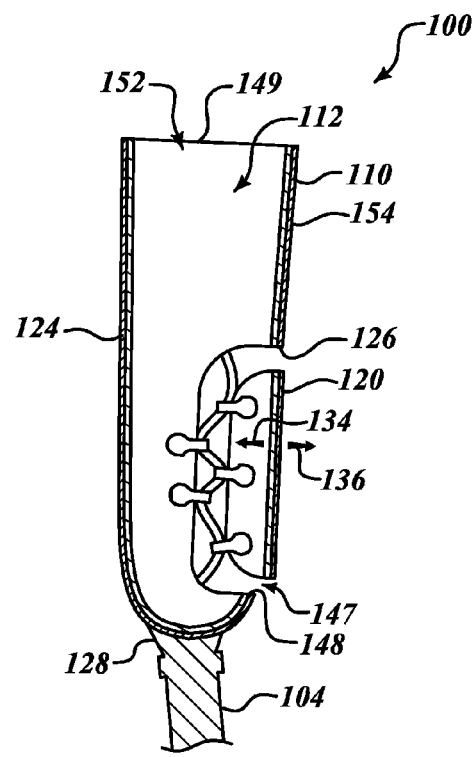

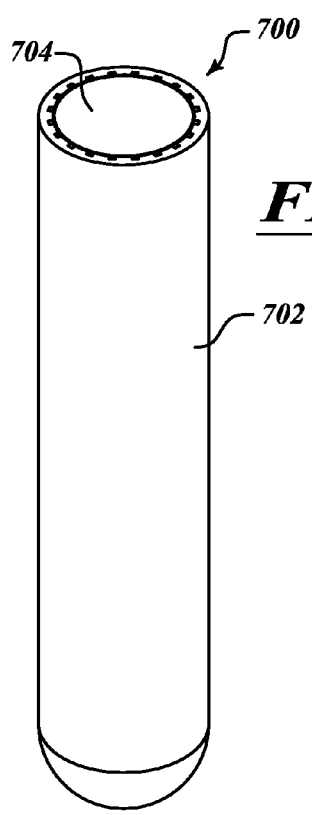
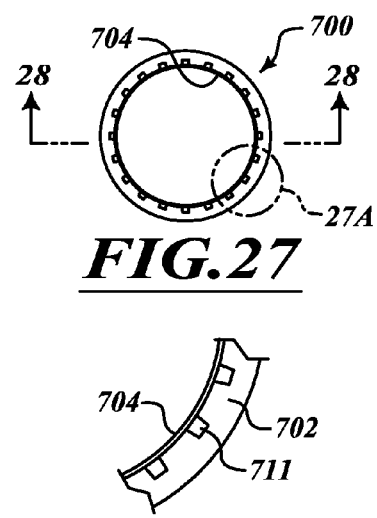
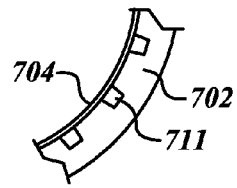
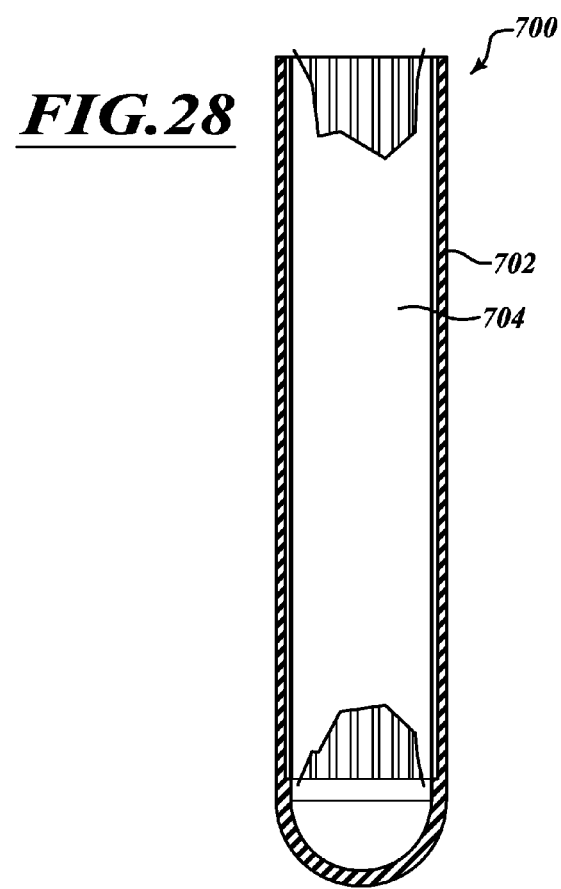
FIG.26
FIG.27
FIG.27A
FIG.28

ADJUSTABLE PROSTHESIS

CROSS-REFERENCE TO RELATED APPLICATIONS

This application claims the benefit under 35 U.S.C. §119(e) of U.S. Provisional Patent Application No. 61/173,205 filed Apr. 28, 2009; U.S. Provisional Patent Application No. 61/173,208 filed Apr. 28, 2009; U.S. Provisional Patent Application No. 61/242,675, filed Sep. 15, 2009; and U.S. Provisional Patent Application No. 61/244,449, filed Sep. 22, 2009. Each of these provisional applications is incorporated herein by reference in its entirety.

BACKGROUND

1. Technical Field

This disclosure generally relates to prostheses and, in particular, adjustable prostheses and/or ventilated prostheses.

2. Description of the Related Art

Amputees often wear prostheses that are uncomfortable, especially if worn for an extended period of time. A prosthetic interface is often the greatest source of discomfort and may also cause a wide range of problems. Poorly fitting sockets of prostheses often cause blisters, ulcers, skin breakdown, infections, and other unwanted skin conditions. Conventional prosthetic liners typically trap moisture (e.g., perspiration) next to the user's skin, contributing to these problems.

A residual limb often changes shape and volume over short periods and long periods of time. These changes can cause problems with the fit of the prosthesis, leading to a wide range of different types of unwanted conditions (e.g., blistering, ulcers, skin breakdown, abrasions, infections, and the like) requiring treatment by a physician, disuse of the prosthesis, and the like.

Conventional prostheses often have a rigid socket lined with a soft liner. The soft liner provides cushioning to enhance comfort. The rigid socket transfers loads to the user's skeleton and provides stability during a stance phase of a gait and suspends the prosthesis during a swing phase of the gait. Unlike the fatty pad under the heel of an intact foot, soft tissue of a residual limb is not well suited to bear loads.

Some sockets have bladder systems that can be inflated to adjust comfort and fit. These bladder systems are often located between a rigid outer shell of the socket and the residual limb. It is often difficult to maintain suitable pressures in the bladder systems because of the repeated applied loads during use, as well as the compliance of the materials forming the bladders. Thus, bladder systems are not suitable for long term use.

To keep a prosthetic's socket fitted to a user, a vacuum can be applied between the user's skin and the socket. Air is drawn from a cavity of the socket using a negative pressure. Unfortunately, negative socket pressures often cause contact dermatitis, verrucous hyperplasia, and significant discomfort. There is a limited number of amputees with chronic residual limb sores for whom the drawbacks of a poorly-fitting socket are outweighed by the benefits of negative pressure therapy to heal the wounds.

If the prosthesis has poor thermal conductivity properties, the prosthesis can function as a heat capacitor that stores thermal energy. This can lead to an elevated residual limb temperature that promotes perspiration and blistering. Unfortunately, these types of prostheses are not suitable for extended use, especially if worn in a relatively hot environment or if worn to perform vigorous exercises.

BRIEF SUMMARY

At least some embodiments disclosed herein involve a prosthesis with an adjustable socket. The adjustable socket can have one or more movable sections for adjusting the fit of the socket. The sections can be moved independently by the user or automatically by a controller. In certain embodiments, the movable sections are in the form of panels that can cooperate with a socket main body to hold the user's residual limb.

In some embodiments, a prosthesis comprises a socket main body, an adjustment panel, and a cavity defined by the socket main body and the adjustment panel. The adjustment panel is movable with respect to the socket main body. The cavity is configured to receive a residual limb.

The prosthesis further includes, in some embodiments, at least one tensioning member held by the socket main body and a plurality of holders of the adjustment panel such that a volume of the cavity is increased or decreased by adjusting the tensile force applied to the tensioning member. A tensioning mechanism can retain and release the tensioning member. In certain embodiments, the tensioning mechanism has a first state for retaining the tensioning member and a second state for allowing the tension member to move to change (e.g., increase or decrease) the volume of the cavity.

In some aspects, the socket main body has a rigid body that defines an edge of a window that surrounds substantially the entire adjustment panel. If the adjustment panel surrounds a distal portion of the user's residual limb, the socket main body can be a generally tubular member with a closed end. The window can be proximate to the closed end. In some embodiments, the edge surrounds the entire adjustment panel and defines a generally rectangular shaped window.

The prosthesis, in some embodiments, securely holds the user's limb. Compressive pressure applied to the limb can be adjusted for enhanced comfort. An air-tight fit can substantially prevent, inhibit, or limit movement of the socket main body with respect to the limb. In other embodiments, compressive forces applied to the limb by the socket keep the prosthesis on the limb. The socket may or may not include an air barrier layer. The compressive forces can be applied by the adjustable panel(s), through suspension devices between the socket and a liner, such as a pin lock, a lanyard, or the like. A wide range of different types of components can cooperate to hold the limb.

In still further embodiments, a prosthesis includes a socket main body, at least one adjustment panel, and a lacing system coupled to both the socket main body and the adjustment panel. The adjustment panel and socket main body cooperate to define a cavity for receiving a residual limb. In certain embodiments, a tensioning mechanism is configured to hold the lacing system to control movement of the adjustment panel with respect to the socket main body when the residual limb is in the cavity. The user can perform a wide range of different activities while the tensioning mechanism and lacing system cooperate to maintain the shape of the cavity.

The lacing system, in some embodiments, includes a first tension member that laces a first adjustment panel to the socket main body such that the first adjustment panel is suspended in a first window. A second tension member laces a second adjustment panel to the socket main body such that the second adjustment panel is suspended in a second window. The lacing system draws vertically extending portions of the panels towards the cavity as tension in the tension members is increased. The top portions and bottom portions of the panels can be pulled against the user's residual limb to provide a uniform compressive pressure.

In some further embodiments, a socket includes a liner system that overlays a substantial portion of an interior surface of a socket main body and an adjustment panel. The liner system can extend across a gap or other type of interface between the socket main body and the panel. This provides support to the user's limb while avoiding pinching or excess compression of the user's skin. In certain embodiments, the liner system overlays substantially all of the interior surface of the socket main body and can be coupled to the socket main body via adhesive, couplers, fasteners, or the like.

In certain embodiments, a prosthesis comprises a socket and an adjustment device for changing the configuration of the socket. The adjustment device includes at least one sensor, a gripper or tensioning mechanism, and a controller.

The controller, in some embodiments, is communicatively coupled to the sensor and the tensioning mechanism. The controller commands the tensioning mechanism to adjust the configuration of the socket based on a signal from the sensor. The tensioning mechanism includes a puller unit and a tensioning member. The puller unit pulls on the tensioning member to reconfigure the socket in response to commands (e.g., signals) from the controller. The controller is programmable to periodically or continuously adjust the configuration of the socket based on a signal (or signals) from the sensor.

In still further embodiments, a prosthesis comprises a socket including a main body, a lacing system, and a panel suspended in an opening of the main body by the lacing system. The lacing system draws an edge of the panel towards the main body to apply a substantially uniform force to the user's limb.

In yet other embodiments, a prosthetic apparatus comprises a liner system. The liner system can provide ventilation while forming a seal (e.g., an airtight seal) with the user's residual limb. In certain embodiments, the liner system includes a water vapor permeable, air barrier layer having a front side and a back side. The front side defines an interior cavity for receiving the residual limb. A ventilation layer is on the back side of the barrier layer. In certain embodiments, the ventilation layer includes a plurality of venting features through which moisture passes to manage moisture at an interface between the user's skin and the liner system.

The barrier layer can allow water vapor to pass therethrough while being substantially impermeable to air. Such a barrier layer can form a generally airtight seal with the user's residual limb positioned in the interior cavity. If a vacuum is drawn between the user's residual limb and the liner system, the vacuum can be maintained without applying significant negative pressures using a pressurization device. In some embodiments, the barrier layer can be permeable to other types of liquids, gases, or the like.

In some other embodiments, a prosthesis is securable to an anatomical feature of a human body and generally includes an adjustable socket and/or a breathable liner system. The anatomical feature can be a residual limb or other type of feature suitable for use with a prosthesis. The prosthesis couples external structures (e.g., a foot, a joint, a pylon, etc.) to the user's body while the liner system serves as an interface between the socket and the skin. The liner system enhances comfort, inhibits or substantially eliminates problems at the interface, and/or promotes healing.

The socket may include a rigid body with indentations to accommodate anatomical features. The indentations can be at specific regions corresponding to specific features (e.g., muscles, tendons, bones, connective tissue, etc.) of a limb. For example, for a transtibial amputee, an indentation can be located to receive the patella tendon. The indentation's size and shape can thus be selected based on the anatomical structure of the residual limb and can help comfortably support the residual limb.

The body of the socket may be a rigid shell, frame, or other structure capable of supporting a significant amount of weight. At least a portion of the socket can be made, in whole or in part, of a rigid material, such as metal (including metal alloys), plastic (e.g., polypropylene), composite material (e.g., laminates, fiber laminates, etc.), or combinations thereof.

A socket, in some embodiments, includes a plurality of movable sections connected to a socket main body with a plurality of tensioning members. The movable sections can be made of a material with a high tensile strength. The socket may also include grippers or locking mechanisms, cams, hooks, or other devices to hold the tensioning members.

In some embodiments, a prosthesis includes a liner system that provides cushion and suspension. The liner system includes a plurality of ventilation features. The ventilation features include vents, holes (e.g., through-holes), channels, passages (e.g., holes, permeable regions, etc.), or combinations thereof and can permit moisture near the skin of the residual limb to be transported away. In some embodiments, an air-tight seal is formed between the skin and the liner system. In certain embodiments, a generally air-tight layer (e.g., a membrane) forms the air-tight seal. The air-tight layer can permit the passage of water vapor therethrough while suspending the socket from the limb.

In further embodiments, a prosthesis includes one or more pressurization devices to move fluid (e.g., heating fluids, cooling fluids, air, vapor, or the like) through, within, and/or across a liner system or other component of a socket. The pressurization devices can include pumps, fans, blowers, or the like.

In still further embodiments, one or more tensioning members can be used to maintain an appropriate volume of an adjustable socket based on a wearer's perception. The socket can be manually or automatically adjusted. In automated embodiments, tension on the tensioning members can be increased or decreased by pulling devices (e.g., small motors). Motors, for example, can rotate to increase or decrease tension in the tensioning members to move a movable section of the socket, thereby adjusting the volume of the adjustable socket. In certain embodiments, the movable section is in the form of a rigid or compliant panel. The panel can surround a portion of the user's body and cooperate with a socket main body to securely hold the residual limb. In other embodiments, the movable section comprises a plurality of panels that are hingedly or otherwise coupled together.

One or more sensors can detect when a change in tension is required or desired. In some embodiments, one or more sensors are mounted within a liner system of the prosthesis. The sensors can be pressure sensors, contact sensors, impedance sensors, or temperature sensors. If the residual limb changes dimensions, the prosthesis can be adjusted based on the changes.

In still further embodiments, a prosthesis can provide adjustability at different locations. An anteriorly adjustable prosthesis includes at least one panel positioned at an anterior region of a socket. In laterally adjustable prostheses, one or more panels can be positioned at the lateral or medial regions of the socket. In posteriorly adjustable prostheses, one or more panels can be positioned at a posterior region of the socket. In distally adjustable prostheses, a distal region of the socket can be formed by a panel. A wide range of different combinations of panel locations can be used to provide any desired adjustability.

A method of adjusting a prosthesis includes detecting a pressure applied by a user on a socket of the prosthesis. The socket includes a movable panel positioned in a window of a socket main body. The movable panel helps support the user's residual limb during use. The configuration of the prosthesis can be adjusted before the prosthesis is worn. A user can configure the prosthesis and then place the prosthesis on a limb.

In yet other embodiments, a method of adjusting a prosthesis includes detecting a characteristic of a limb. The socket includes a panel that is movable to adjust a volume of a cavity of the socket. The method further includes adjusting the position of the panel based on the characteristic of the limb detected by at least one sensor. The detected characteristic of the limb can include, without limitation, a temperature of the limb, a volume of the limb, location of tissue, and the like. In certain embodiments, the socket supports a significant portion of the user's body mass while the panel is adjusted. The socket can be reconfigured by moving one or more tensioning members. In some embodiments, one or more sensors carried by the socket detect the characteristic. One or more signals can be sent from the sensors to a controller commanding the socket.

Sensors can be installed in liner systems, sockets, or components of prosthesis systems and can be used to maintain appropriate volume of an adjustable socket based on, without limitation, the wearer's perception, characteristics of the residual limb, the condition of the residual limb, or combinations thereof. Automating the process by which the tension on the tensioning members is increased or decreased could be accomplished by tensioning mechanisms. The sensors can be used to detect when a change in tension is required to rotate a motor of the tensioning mechanism. Motors can rotate to increase or decrease in tension to move the adjustable panel, thereby adjusting the volume of the adjustable socket.

BRIEF DESCRIPTION OF THE SEVERAL VIEWS OF THE DRAWINGS

In the drawings, identical reference numbers identify similar elements or acts.

FIG. 2 is a back view of the prosthesis of FIG. 1.

FIG. 3 is a cross-sectional view of a portion of the prosthesis of FIG. 2 taken along a line 3-3.

FIG. 26 is a perspective view of a liner system with a plurality of vertically extending channels.

FIGS. 27 and 27A are plan views of the liner system of FIG. 26.

FIG. 28 is a cross-sectional view of the liner system of FIG. 26 taken along a line 28-28 of FIG. 27. A membrane is shown partially removed.

DETAILED DESCRIPTION

The terms "proximal" and "distal" are used to describe the illustrated embodiments and are used consistently with a description of non-limiting exemplary embodiments and applications. The terms "proximal" and "distal" are used in reference to the user's body when the user wears a prosthesis, unless the context clearly indicates otherwise. For example, a proximal feature of a prosthesis is closer to a user's torso than a distal feature of the prosthesis. It will be appreciated, however, that the illustrated embodiments and features can be located or oriented in a variety of desired positions.

Figure 1:
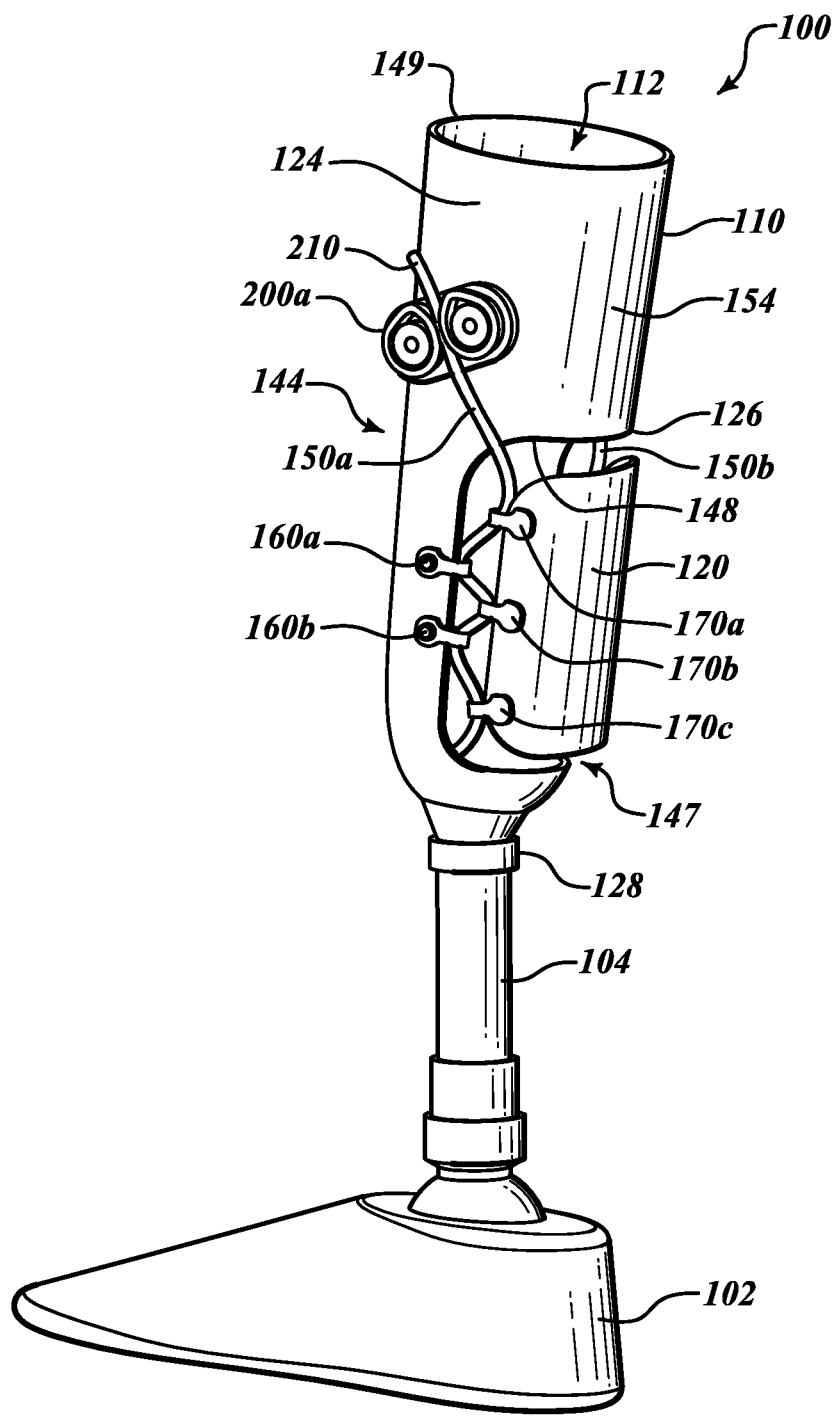
FIG. 1 is a perspective view of a prosthesis for attaching below a knee.

FIGS. 1-3 show a prosthesis 100 for supporting a user. The prosthesis 100 includes a foot 102, a pylon 104, and a socket 110. The pylon 104 extends between the foot 102 and the socket 110. To wear the prosthesis 100, a residual limb can be inserted into a cavity 112. The socket 110 is connected to an upper end 128 of the pylon 104 and remains securely coupled to the residual limb as the foot 102 is repeatedly brought into contact with a support surface. The illustrated prosthesis 100 is in the form of a below the knee prosthesis for receiving a below the knee residual limb.

The socket 110 can be adjusted to alter the fit of the prosthesis 100 to, for example, enhance comfort, fit, performance (e.g., stability, balance, etc.), reduce unwanted conditions (e.g., ulcers, blisters, etc.), promote healing, or the like. The socket 110 includes an adjustment panel 120 positioned within a window 126. The panel 120 can be moved with respect to a socket main body 124 to change the characteristics (e.g., shape, volume, dimensions, etc.) of the cavity 112. Adjustments can be based on, without limitation, forces, pressures (e.g., pressure applied by the user), characteristics of the residual limb (e.g., shape, size, limb volume, skin temperature, tissue composition of the residual limb, etc.), conditions of the residual limb (e.g., locations of ulcers, blisters, lesions, etc.), or the like. If the residual limb changes shape over time, the socket 110 can be reconfigured any number of times to accommodate the shape changes.

The panel 120 can be moved inwardly, as indicated by an arrow 134 of FIG. 3, and outwardly, as indicated by an arrow 136 of FIG. 3. For example, the panel 120 can be moved inwardly or outwardly to decrease or increase, respectively, the volume of the cavity 112. The panel 120 can be reoriented and repositioned any number of times in this manner.

A socket edge 148 defines the window 126 and can be spaced apart and adjacent to the periphery of the panel 120. In some embodiments, including the illustrated embodiment, the edge 148 is a continuous edge that surrounds the entire panel 120. A gap 147 is defined between the panel 120 and the edge 148. In certain embodiments, including the illustrated embodiment, the gap 147 has a generally uniform width. In other embodiments, the gap 147 has a varying width.

Referring to FIG. 3, a rim or upper portion 149 of the socket main body 124 defines an entrance 152 of the socket 110. The upper end of the window 126 is spaced apart from the entrance 152. A sidewall 154 can extend between the window 126 and the rim 149. As such, only the distal portion of the limb engages the panel 120. The sidewall 154 has a generally tubular shape and surrounds a proximate portion of the limb. The height of the sidewall 154, the overall dimensions of the socket main body 124, and the dimensions and configuration of the panel 120 can be selected based on the shape, dimensions, and/or tissue composition of the residual limb.

Referring again to FIG. 1, the socket 110 includes a lacing system 144. The lacing system 144 includes a pair of tensioning members 150a, 150b (collectively "150") that lace together the panel 120 and the socket main body 124. The tensioning member 150a is held by each holder 160a, 160b of the socket main body 124 and is held by each holder 170a, 170b, 170c of the panel 120. The illustrated tensioning member 150a travels alternatingly between the holders 160, 170 and forms a generally zigzag configuration. The illustrated tensioning member 150a extends across the gap 147 and connects most of the vertical length of the panel 120 to the socket main body 124. The panel 120 can be pulled inwardly by a generally uniform force applied along the vertical length of the panel. This ensures that a generally uniform pressure is applied to a posterior section of the residual limb. The tension in the tensioning member 150a can thus be increased or decreased to provide posterior adjustability.

The tensioning members 150a, 150b can include, but are not limited to, cables, cords, or other types of flexible elongate members capable of withstanding relatively large tensile forces. The tensioning member 150a may be a flexible cable capable of assuming highly curved configurations and can be made, in whole or in part, of polymers, plastic, metal (e.g., braided metal), or the like. In some embodiments, the tensioning member 150a is a metal cable (e.g., steel cable) with a polymer coating. The polymer coating can reduce or limit frictional interaction with the holders 160, 170. In certain embodiments, the tensioning members 150 comprise an electroactive material. For example, the tensioning members 150 can be a cable made of an electroactive polymer that can exhibit large strains when subjected to a varying voltage. The electroactive polymer cables can thus extend or contract using varying voltages, enabling volume changes of the prosthesis 100.

The holders 160, 170 can include, without limitation, hooks, grommets, eyelets, loops, or other features for holding or receiving at least one tensioning member. Holders 160, 170 can have apertures (e.g., closed apertures, open apertures such as U-shaped channels, or the like). The illustrated holders 160, 170 include generally U-shaped hooks for holding a tensioning member passing therethrough and are coupled to the socket main body 124 and the panel 120. In other embodiments, sections of the panel 120 can form the holders. For example, holders can be through-holes formed in the panel 120. A tensioning member can pass through the through-holes. Grommets or other types of reinforcements can be incorporated into the panel to reinforce the material surrounding the through-holes.

The panel 120 can have a shape generally corresponding to a portion of the residual limb to closely surround the residual limb. The illustrated the panel 120 has a generally arcuate shape and may be rigid, semi-compliant, or compliant. In rigid embodiments, the panel 120 can be made of metal, composite materials, polymers, or the like. In semi-compliant embodiments, the panel 120 can have a multi-layer construction. A first portion of the panel can be a rigid structure, for example, made of metal. Another portion of the panel can be made of a compliant material, such as a compliant polymer, rubber, elastomer, or the like. In compliant embodiments, the panel 120 can readily deform to the shape of the residual limb. Compliant panels can be formed of a highly compliant or drapable material, such as a fabric, a flexible sheet, or the like. To enhance ventilation, the panel 120 can comprise a breathable material.

Figure 4:
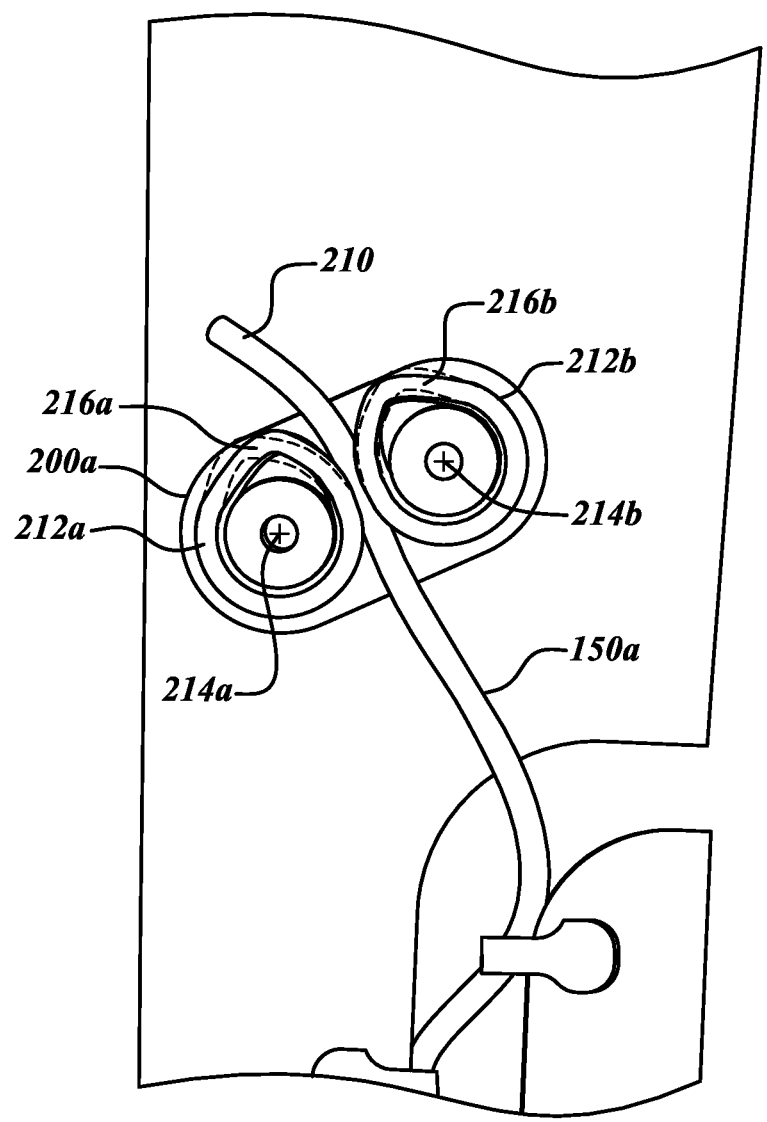
FIG. 4 is a detailed view of a portion of the prosthesis of FIG. 1.

Referring to FIGS. 1 and 4, a tensioning mechanism 200a selectively holds the tensioning member 150a. To move the panel 120 inwardly, a user can pull an end 210 of the tensioning member 150a. Once the panel 120 reaches the desired position, the tensioning member 150a can be released by the user. The tensioning mechanism 200a holds the tensioning member 150a to limit the outward movement of the panel 120.

The tensioning mechanism 200a of FIG. 4 includes a pair of camming members 212a, 212b (collectively "212"). The camming members 212 are movable from a locked position (illustrated) and a release position (shown in dashed line). The camming members 212a, 212b rotate about axes of rotation 214a, 214b, respectively. When the tensioning member 150a is tensioned, the tensioning member 150a pulls the camming member 212a clockwise and pulls the camming member 212b counterclockwise. Eccentric portions 216a, 216b cooperate to pinch and hold the tensioning member 150a. This is shown in FIG. 4.

When the user pulls the end 210, the tensioning member 150a rotates the camming member 212a counterclockwise and the camming member 212b clockwise to the release positions. When the tensioning member 150a is released by the user, it once again rotates the camming member 212a clockwise and the camming member 212b counterclockwise. In this manner, the tensioning mechanism 200a can self-lock.

Of course, the user can manually move the camming members 212 without pulling the tensioning member 150.

To manufacture the prosthesis 100 of FIGS. 1-4, the socket main body 124 can be formed to fit the wearer. To form the socket main body 124, a prosthetist can produce a positive model of the residual limb by casting the residual limb, making a digital scan and utilizing computer aided manufacturing technology to fabricate the positive model, or the like. Computer aided design/computer aided manufacturing may also be used to fabricate the positive mold, either in a prosthetics clinic or at a central fabrication shop. After forming the positive model, the prosthetist or a prosthetics technician can mold material around the positive mold. The molding material can be a thermoplastic, thermoset, or the like. If the molding material is a thermoplastic material, the thermoplastic material can be heated to shape it around the positive mold. The thermoplastic material can be cooled to a final shape. If the molding material is a thermosetting material, the molding material can be molded around the mold and subsequently cured. For example, the molding material can be laminae that are wrapped around the positive model. The laminae can be cured and the laminate can be removed from the positive mold. In various embodiments, a shell of the socket main body 124 can be made, in whole or in part, of plastics, composite materials, metals, or combinations thereof. Plastics can include polypropylene, polyester, or other plastics with suitable mechanical properties (e.g., compressibility, yield strength, ultimate strength, modulus of elasticity, etc.). Composite materials include fiber reinforced composites, laminates, or the like. Metals include metal alloys.

After forming the socket main body 124, a section of the socket main body 124 can be removed by cutting out the window 126. To ensure that the socket main body 124 will support the amputee, the window 126 can placed over the general areas of soft tissue as opposed to bony areas on the residual limb. The window 126 can be any size hole selected by the user. Of course, the socket main body 124 should be large enough to support the necessary mass of the user. The socket 110 can be shaped and configured such that most of the user's body mass is supported on desired regions of the residual limb.

Figure 5:
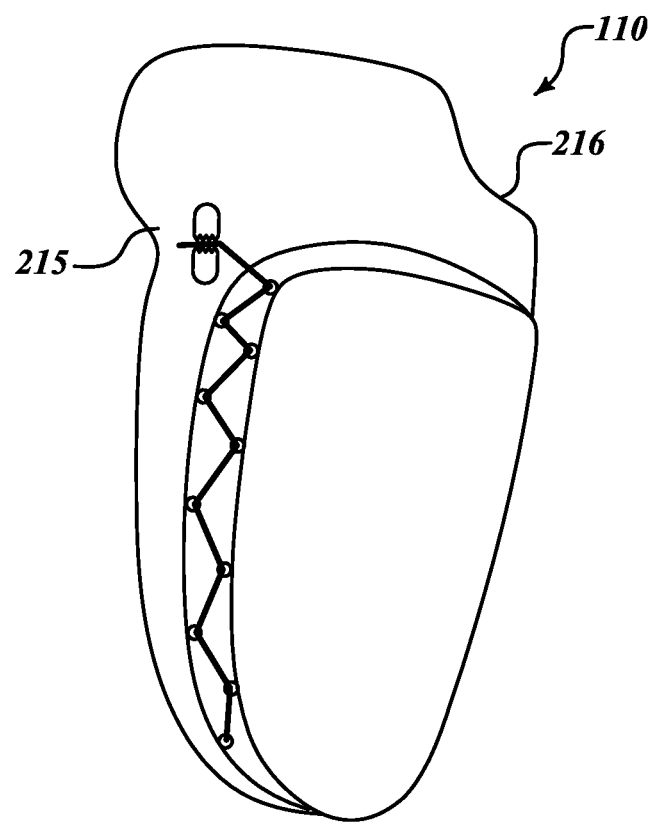
FIG. 5 is a side elevational view of a socket, in accordance with one embodiment.

FIG. 5 is a side elevational view of an adjustable below the knee socket 110 with an indentation 215. The indentation 215 corresponds to the patella tendon on a residual limb supported in the socket 110. Relief cutouts 216 permit the hamstrings to contract. A wide range of different types of indentations and/or cutouts can be formed in the socket 110. The configurations, shapes, dimensions, and locations of the indentations and/or cutouts, or other features, can be selected based on the anatomy of the residual limb.

Figure 6:
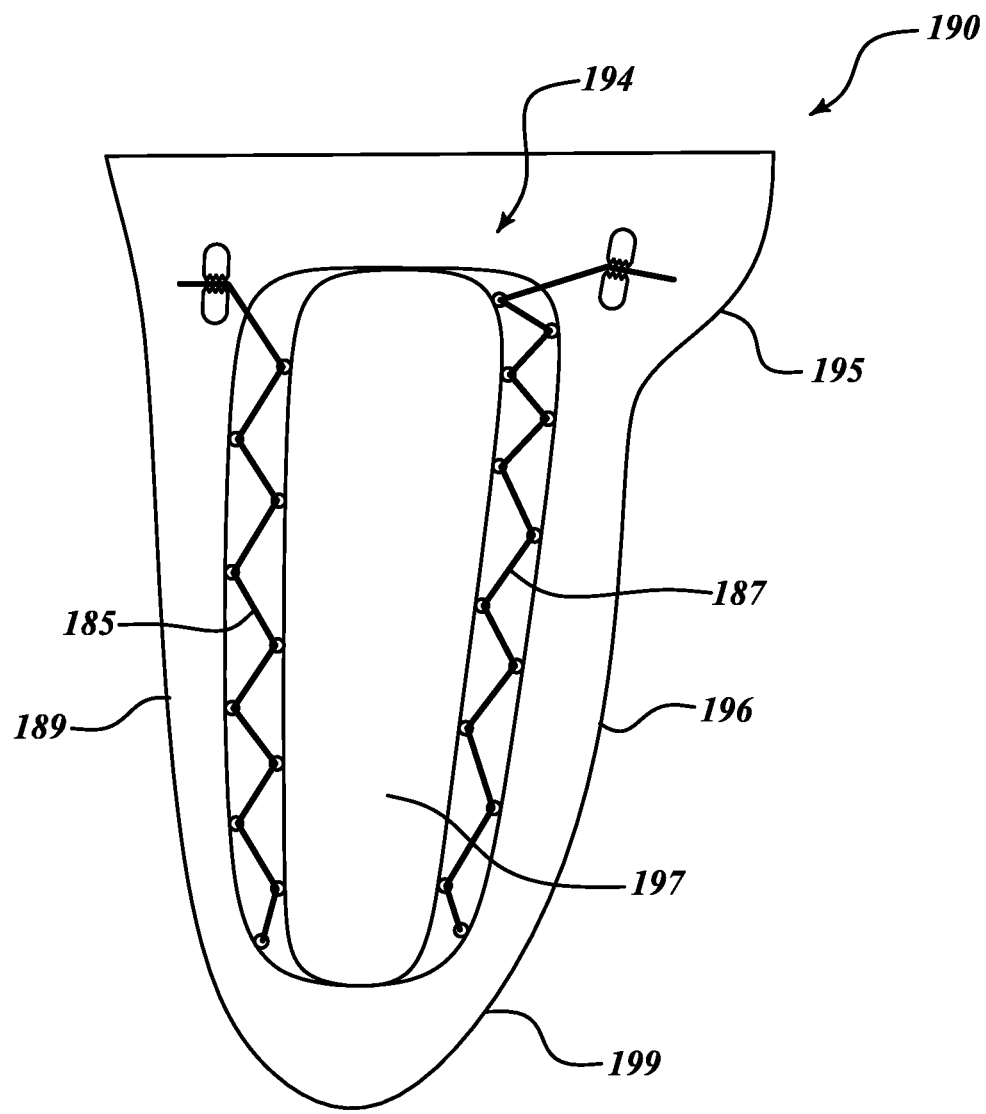
FIG. 6 is a side elevational view of a socket with an indentation, in accordance with one embodiment.

FIG. 6 is a side elevational view of an adjustable above the knee socket 190 that provides anterior and posterior support. The socket 190 includes a socket main body 196 with an adjustable panel 197 that is connected to the socket main body 196 by a lacing system 194. The lacing system 194 includes a first tensioning member 185 on one side of the panel 197 and another tensioning member 187 on the other side of the panel 197. The tensioning members 185, 187 extend upwardly along the vertical edges of the panel 197.

The socket main body 196 is formed with an indentation 195 to aid in loading bodyweight. The indentation 195 can come in contact with the ischium of the wearer in order to help support the residual limb. The anterior support region 189 prevents excessive bending of the socket 190.

Figure 7:
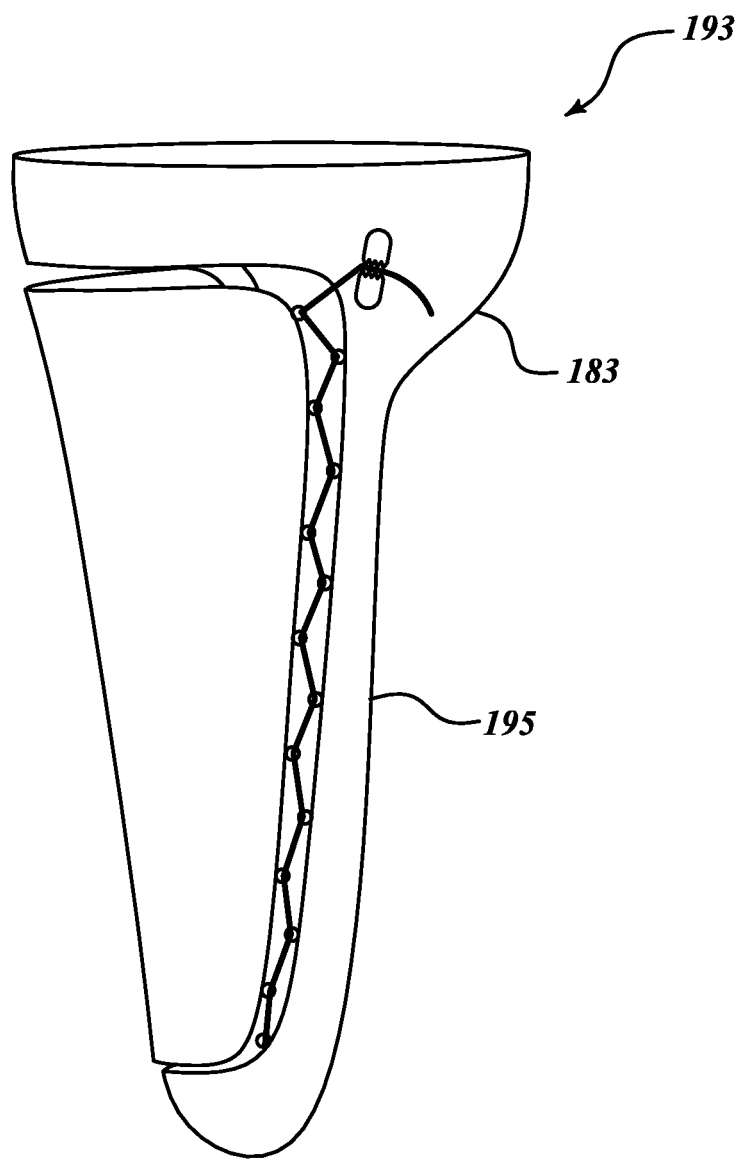
FIG. 7 is a side elevational view of a socket, in accordance with another embodiment.

FIG. 7 is a side elevational view of another above the knee prosthesis 193. A socket main body 195 is formed with an indentation 183 to aid in loading bodyweight. The indentation 183 contacts the ischium of the wearer in order to help support the residual limb.

Figure 8:
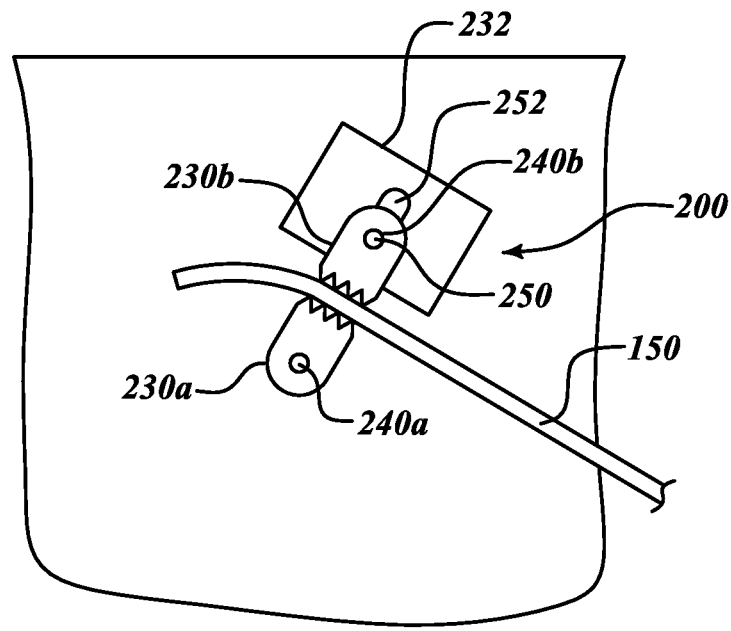
FIG. 8 is a side elevational view of a tensioning mechanism in a closed configuration.
Figure 9:
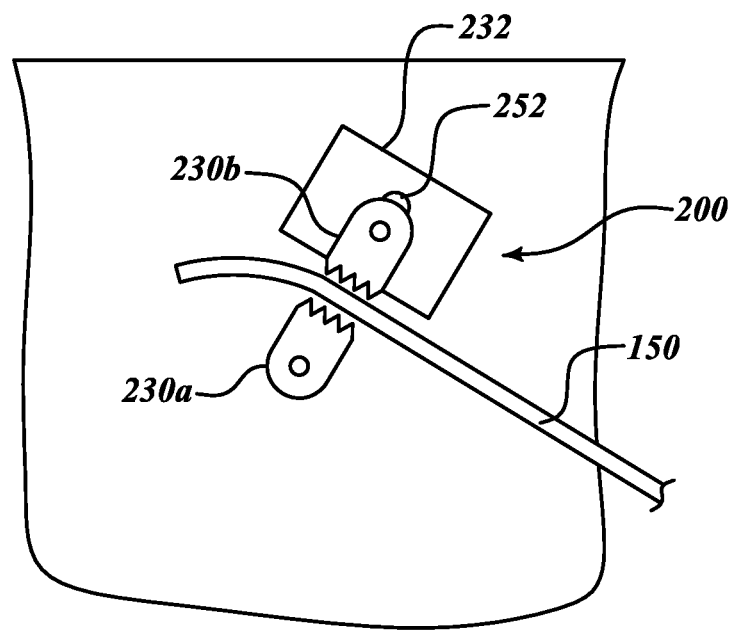
FIG. 9 is a side elevational view of the tensioning mechanism of FIG. 8 in an open configuration.

FIGS. 8 and 9 show an embodiment of a tensioning mechanism 200. FIG. 8 shows the tensioning mechanism 200 in a first state for retaining the tensioning member 150. FIG. 9 shows the tensioning mechanism 200 in a second state for allowing movement of the tensioning member 150. The tensioning mechanism 200 includes a pair of grippers 230a, 230b and an actuator 232. The actuator 232 moves the gripper 230b towards the gripper 230a to compress and hold the tensioning member 150.

The grippers 230a, 230b can pivot about hinges 240a, 240b to ensure proper contact. A shaft 250 of the hinge 240b can be moved along a slot 252 of the actuator 232. The actuator 232 can move the gripper 230b away from the gripper 220a to free the tensioning member 150 and can include any number of solenoids, power supplies (e.g., batteries, power sources, etc.), mechanical clamps, motors, or the like.

The tensioning mechanism 200 can be controlled manually or by another component, such as a controller (e.g., a controller coupled to or integrated into the prosthesis, an external controller, a network, a computer, or the like). The controller can operate the tensioning mechanism 200 based on programs, feedback from the socket (e.g., signals from sensors in the socket), control algorithms, or the like. In other embodiments, the actuator 232 can include an internal controller.

A wide range of other types of tensioning mechanisms can be employed with the prostheses disclosed herein. Non-limiting exemplary tensioning mechanisms can include, without limitation, clamps (e.g., mechanical clamps, electro-mechanical clamps, pneumatic clamps, etc.), puller units, or the like. The configuration and design of the tensioning mechanisms can be selected based on the forces needed to reconfigure the socket, forces needed to keep the socket in the desired configuration, or the like.

Figure 10:
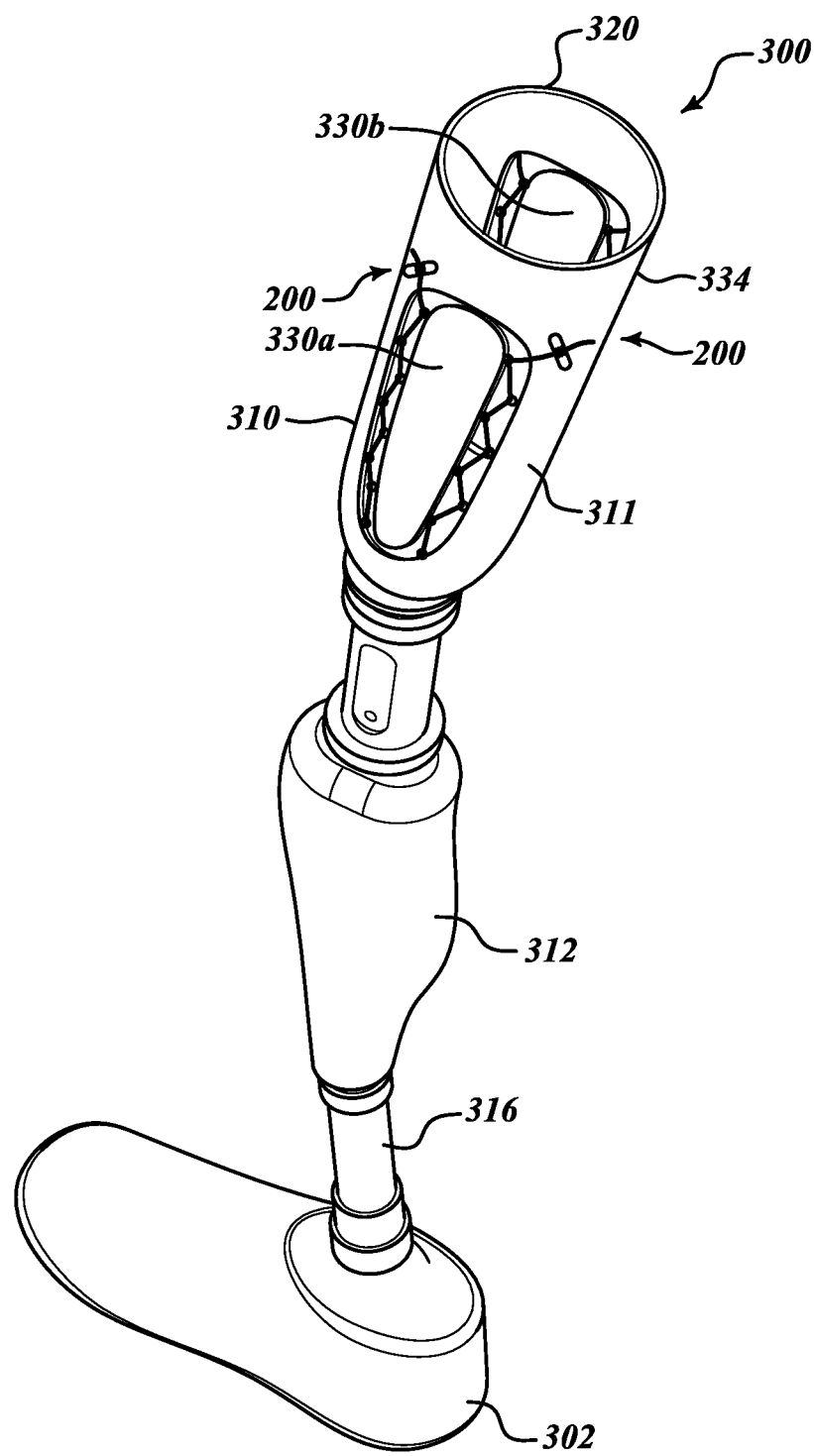
FIG. 10 is a perspective view of a prosthesis for attaching above a knee.
Figure 11:
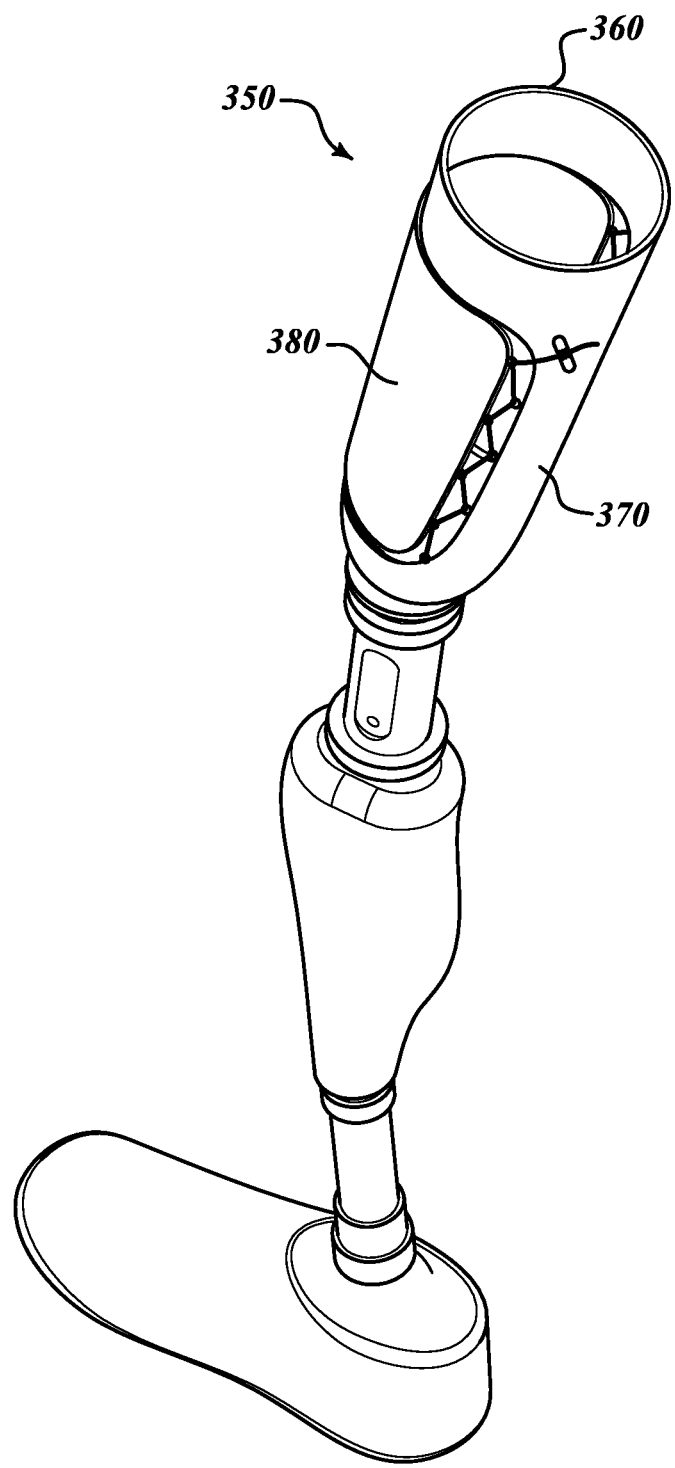
FIG. 11 is a perspective view of an above the knee prosthesis.

FIGS. 10 and 11 show prostheses that are generally similar to the prosthesis 100 discussed in connection with FIGS. 1-4, except as detailed below.

FIG. 10 shows a prosthesis in the form of an above the knee prosthesis 300. The prosthesis 300 has anterior and posterior supports 310, 311 and generally includes a foot 302, a prosthetic knee 312, and a pylon 316 between the foot 302 and the knee 312. A socket 320 is coupled to the prosthetic knee 312.

The socket 320 includes a plurality of independently adjustable panels 330a, 330b (collectively "330"). The panels 330 can cooperate to substantially prevent, inhibit, or limit excessive deformation or excessive bending in the socket 320. The illustrated panels 330 are generally located on the medial, lateral sides of a socket main body 334 to maintain enough rigidity of the socket 320 to support the wearer during walking. Of course, anterior and posterior regions 310, 311 provide most of the support during walking, running, or other types of strenuous exercise.

FIG. 11 shows a prosthetic in the form of an above the knee prosthesis 350 with anterior adjustability. The prosthesis 350 includes a socket 360 with posterior support 370 and an adjustable anterior panel 380. The panel 380 is positioned to cover soft tissue on the anterior region of the residual limb.

Figure 12:
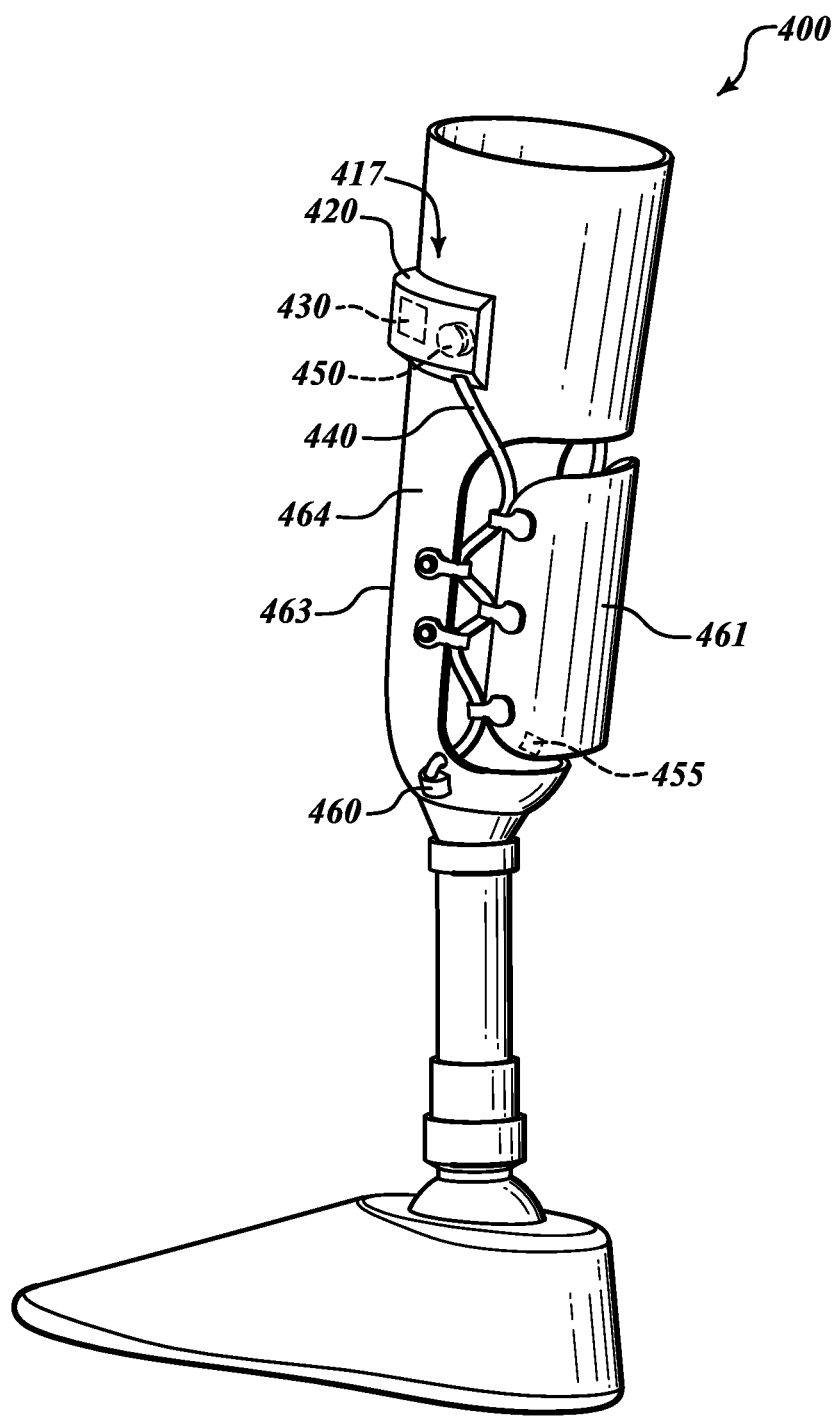
FIG. 12 is a prosthesis with an automatically adjustable socket.

FIG. 12 shows a prosthesis 400 that can be automatically reconfigured. The prosthesis 400 includes an adjustment device 417 including a tensioning mechanism 420 and a controller 430 (illustrated in dashed line). The controller 430 can command the tensioning mechanism 420 to make volumetric adjustments. One or more sensors 455 (shown in dashed line) can be communicatively coupled to the controller 430. The controller 430 can receive signals from the sensors and send signals to components (e.g., motors) of the tensioning mechanism 420.

The illustrated tensioning mechanism 420 includes a puller unit 450 (illustrated in dashed line) that can tension or loosen the tensioning member 440. The puller unit 450 can include one or more motors, spools, spindles, or the like.

The controller 430 can generally include, without limitation, one or more central processing units, processing devices, microprocessors, digital signal processors (DSP), application-specific integrated circuits (ASIC), and the like. To store information, controllers also include one or more storage elements, such as volatile memory, non-volatile memory, read-only memory (ROM), random access memory (RAM), and the like. Example displays of the controller include, but are not limited to, LCD screens, monitors, analog displays, digital displays (e.g., light emitting diode displays), or other devices suitable for displaying information. The display can indicate the settings of the socket, force profiles, data collected by sensors (e.g., pressure applied by user, forces applied to the tensioning member 440, or the like), or any other information. The controller 430 can store information. The term "information" includes, without limitation, one or more programs, executable code or instructions, operating instructions, combinations thereof, and the like. The controller 430 can store a wide range of different programs. The programs can include programs for reconfiguring the socket, controlling a pressurization device, controlling thermal elements, or the like.

The sensors can be incorporated into a socket 463, into a liner system, or other components. If the sensors are part of a separate component (e.g., a sleeve wearable on the residual limb), the sensors can wirelessly communicate with the controller 430. If the sensors are mounted on, embedded in, or otherwise coupled to the socket 463, the sensors can be connected via wires or wirelessly to the controller 430.

FIG. 12 also shows a sensor in the form of a load cell 460 that monitors (e.g., continuously, intermittently, etc.) the tension in the tensioning member 440. Any number of load cells can be used. For example, if a lacing system has a plurality of tensioning members, each tensioning member can be monitored with a different load cell carried on, for example, the panel 461 or the socket main body 464.

Sockets can be formed of an actuating material that moves between any numbers of configurations. The actuating material can include, without limitation, a shape memory alloy (e.g., Nitinol), shape memory polymers, electro-active polymers, piezoelectric materials, or combinations thereof. Some shape memory materials can change states (e.g., preset configurations) in response to temperature changes, applied electrical currents, or combinations thereof and can have any number of preset configurations to accommodate the user's limb. In some embodiments, the actuating material can have a first configuration for performing one activity (e.g., walking) and another configuration for performing another activity (e.g., walking, jogging, etc). In other embodiments, the actuating material has a first configuration when the residual limb has a first shape, and another configuration when the residual limb has a second shape. Because a residual limb's shape may change over time, the actuating material can be used to adjust the shape of the prosthesis to enhance the fit. The controller 430 of FIG. 12 can be used to adjust the shape of the socket 410 or the panel 461 using the various actuating materials.

In some methods of adjusting the prosthesis 400 of FIG. 12, a pressure applied by a user on the socket 463 is detected by the sensor 455. The position of the panel 461 is adjusted based on the detected pressure. During repositioning of the panel 461, a significant portion of the user's mass (e.g., substantially all the user's mass, at least 50% of the user's mass, or the like) is supported by the socket main body 464. This allows adjusting of the prosthesis 400 without removing the prosthesis 400.

Figure 13:
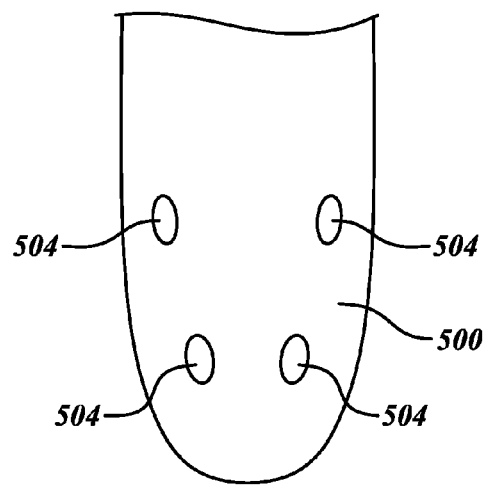
FIG. 13 is an elevational view of a limb carrying a plurality of sensors.
Figure 14:
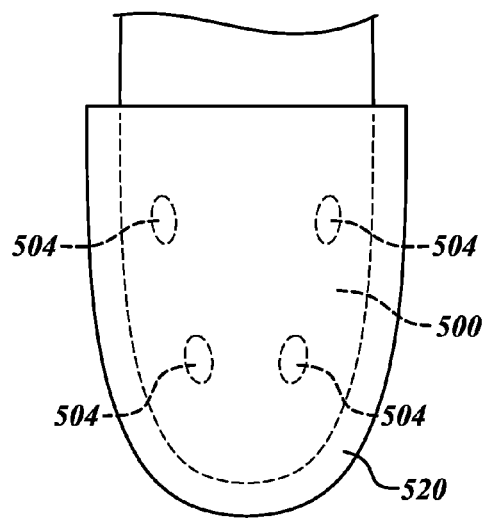
FIG. 14 is an elevational view of the limb of FIG. 13 positioned in a socket.

Referring to FIGS. 13 and 14, a residual limb 500 can carry surface mounted sensors 504. The sensors 504 are adhered directly to the skin of the residual limb 500. FIG. 14 shows the residual limb 500 positioned in a socket 520. The number, size, and position of the sensors can be selected based on the characteristics that are going to be detected. The detected characteristic can be limb volume, tissue type, limb temperature, impedance of the limb, or the like. The illustrated four spaced apart sensors 504 are electromyogram (EMG) sensors.

If the prosthesis includes a controller, the controller can receive signals from the sensors and then adjust the socket volume. The sensors can also be part of a sleeve that is worn on a residual limb and can wirelessly communicate with the controller. If sensors (e.g., sensors 500) are mounted on, embedded in, or otherwise coupled to a socket, the sensors can be connected via wires or wirelessly to the controller.

With continued reference to FIGS. 13 and 14, the sensors 540 can be pressure sensors to detect the changes in pressure. As the residual limb 500 shrinks, the pressures within the socket 520 would decrease, requiring an adjustment panel to be moved in by increasing tension on tensioning members.

Bioimpedance sensors can detect volume changes of the residual limb 500. The residual limb 500 volume can shrink as extracellular fluid is pushed out of it. The bioimpedance can increase as extracellular fluid decreases. Therefore, there is an indirect inverse linear correlation between the residual limb volume and bioimpedance. The correlation can be used to determine a desired configuration of the socket 520. The bioimpedance can thus be monitored using sensors 504 in the form of bioimpedance sensors to dynamically reconfigure the socket 520.

The sensors 504 can be in the form of shear sensors positioned to measure shear forces. As the residual limb 500 shrinks, the overall fit of the socket 520 can be loosened. The result is increased movement between the residual limb 500 and the socket 520 and, thus, increased shear forces on the residual limb 500. The shear forces can be reduced or eliminated by moving an adjustment panel.

The sensors 504 can also be in the form of temperature sensors. Temperature sensors 504 can detect the temperature of the residual limb 500. Blood perfusion to the skin is a natural thermoregulatory response to increased skin temperature. The greater the skin temperature, the more blood goes to the skin surface to dissipate heat. Therefore, residual limb 500 volume increases as skin temperature increases, requiring an adjustment panel to be moved out by decreasing tension on tensioning members.

An automated tensioning mechanism can receive signals from the sensors (e.g., pressure sensors, bioimpedance sensors, shear sensors, temperature sensors, or the like) to automatically control the motors used to position the panels. A controller can be used to process the signals and to send signals to any number of motors to accurately position the panels before, during, or after use.

Figure 15:
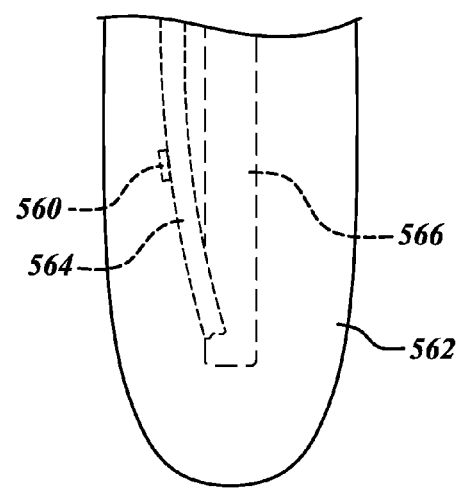
FIG. 15 is an elevational view of an implanted sensor in a limb.

FIG. 15 shows an implantable sensor 560 (shown in dashed line) in a limb 562. The illustrated sensor 560 detects one or more characteristics of the limb 562. If the sensor 560 is a pressure sensor, it can detect pressure changes in tissue. The sensor 560 can be implanted in or proximate to a muscle 564 (shown in dashed line) or positioned proximate to a bone 566

(shown in dashed line) to detect pressure. The sensor 560 can be positioned in a muscle belly to detect changes in intramuscular pressure. Any number of implantable sensors can be located in, proximate to, or mounted on muscles, tendons, or other tissue and can measure signals (e.g., electromyogram signals), tissue pressures, or other metrics. Because a residual limb can change volume, for example, during a step, implantable sensors may be sensitive enough to provide a signal to change socket volume during the step or after the step is completed.

Figure 16:
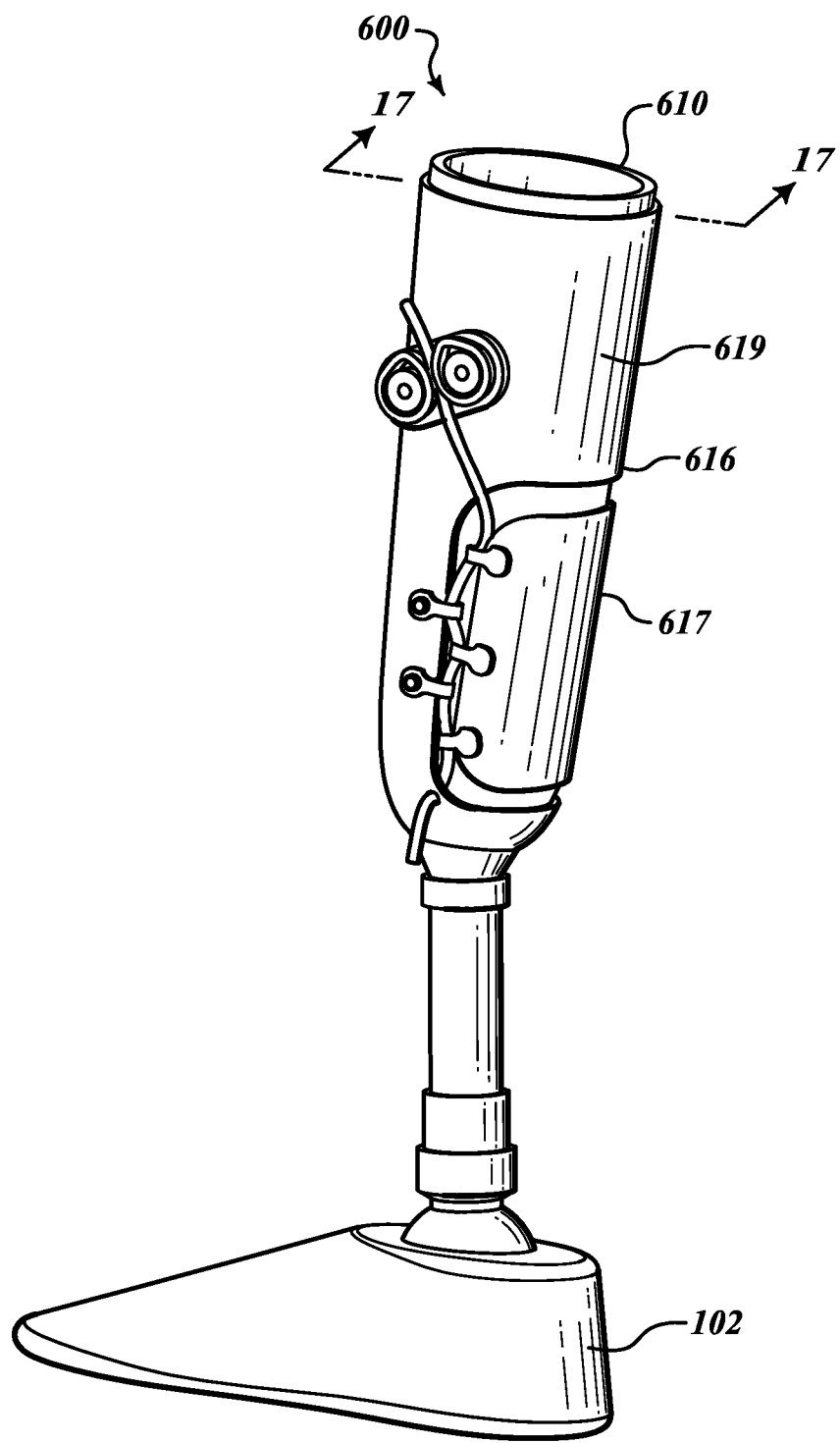
FIG. 16 is a perspective view of a below the knee prosthesis with a liner system.
Figure 17:
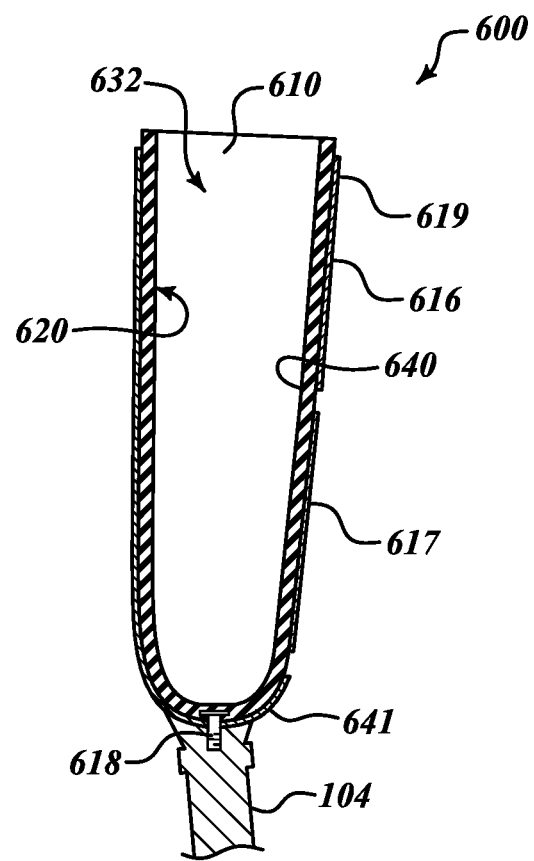
FIG. 17 is a cross-sectional view of a portion of the prosthesis of FIG. 16 taken along a line 17-17.
Figure 18:
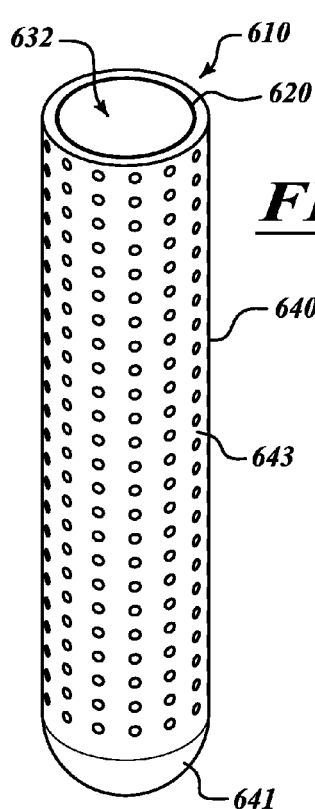
FIG. 18 is a perspective view of a liner system, in accordance with one embodiment.
Figure 19:
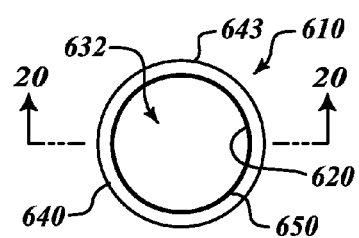
FIG. 19 is a plan view of the liner system of FIG. 18.
Figure 20:
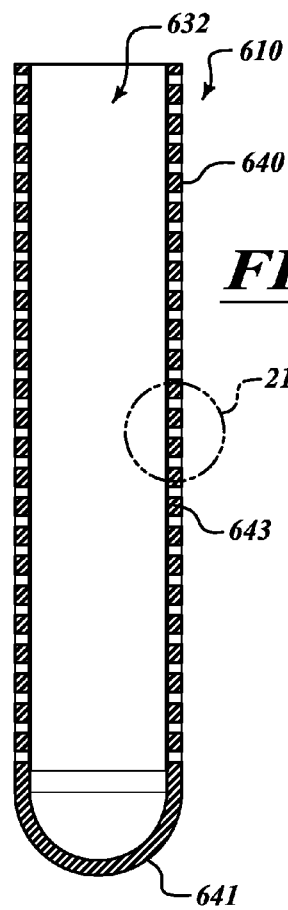
FIG. 20 is a cross-sectional view of the liner system of FIG. 18 taken along a line 20-20 of FIG. 19.
Figure 21:
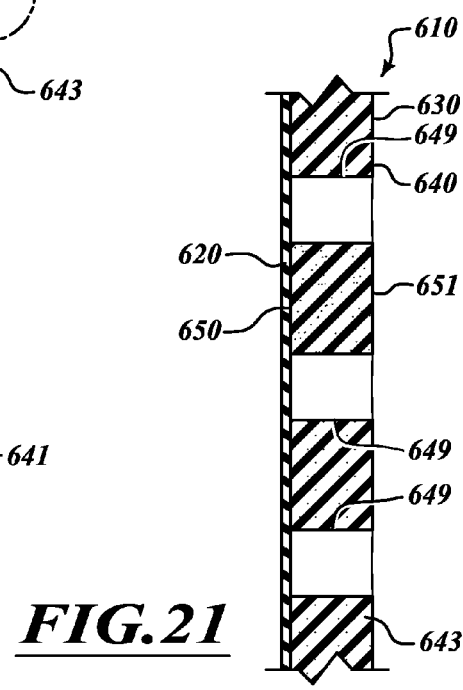
FIG. 21 is a detailed view of a portion of the liner system of FIG. 20.
Figure 22:
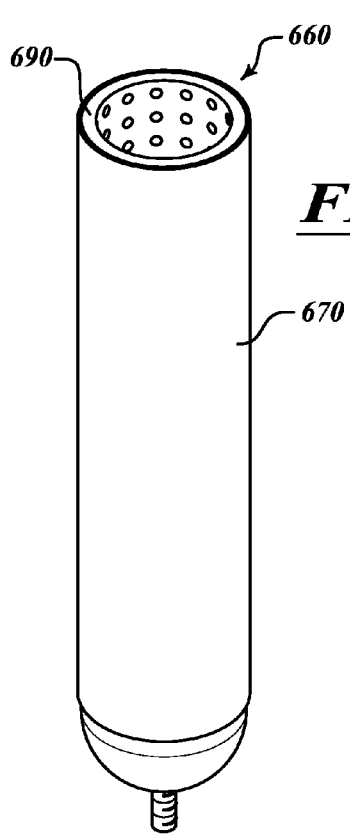
FIG. 22 is a perspective view of a liner system, in accordance with another embodiment.
Figure 23:
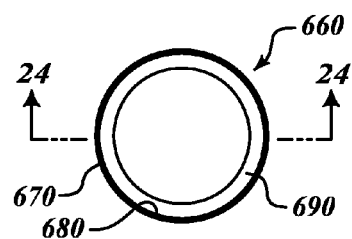
FIG. 23 is a plan view of the liner system of FIG. 22.
Figure 24:
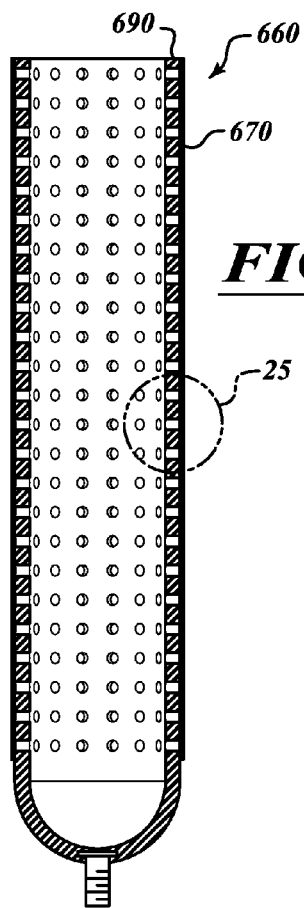
FIG. 24 is a cross-sectional view of the liner system of FIG. 22 taken along a line 24-24 of FIG. 23.

FIGS. 16 and 17 show a lower limb prosthesis 600 for a below the knee amputee. The prosthesis 600 includes a liner system 610. The liner system 610 can be coupled to a socket 619 by a coupler 618 and extends across an interface (illustrated as a gap) between a socket main body 616 and a panel 617. The coupler 618 can be a pin lock system and/or can include one or more pins (e.g., pins with ridges), threaded fasteners, snap fittings, lanyards, or the like.

To control moisture, the liner system 610 includes an inner layer that defines an interface with the residual limb and allows for moisture removal. The inner layer can be made of a material that is generally airtight and that allows the passage of water vapor therethrough. Such inner layers can be formed, in whole or in part, of a polyestherester membrane or other barrier layers. In some embodiments, the membranes are water vapor permeable, air barrier layers that allow water vapor to pass therethrough. The barrier layer also forms a generally airtight seal with the user's skin.

The barrier layers can be made of tightly-woven fibers. The fibers can have sections that are hydrophobic and hydrophilic. As water vapor comes in contact with a hydrophilic section, it is sucked into the membrane only to come in contact with the hydrophobic section which pushes the water vapor out of the membrane on the other side. Vapor permeability increases with temperature and humidity gradients on either side of the membrane. That is, if it gets hotter or more humid on the inside of the membrane, more vapor can be transported to the outside of the membrane. Exemplary membranes can be made, in whole or in part, of SYMPATEX® or similar material.

To provide temperature control, the liner system 610 can include one or more thermal elements. The thermal elements can be Peltier devices. Peltier devices can be solid state components which become hot on one side and cool on an opposing side, depending on a direction of current passed therethrough. By simply selecting the direction of current, Peltier devices can be employed to or cool for a desired length of time. In other embodiments, the thermal elements are resistive heaters. In yet other embodiments, the thermal elements are channels through which a working fluid (e.g., air, water, etc.) flows. Heated fluid can be passed through the channels for a heating period, and a chilled fluid can be passed through the channels for a cooling period. The position, number, and type of thermal elements can be selected based on the desired temperature profile of the user's limb. By way of example, if the prosthesis is used in cold environments, the thermal elements can heat the limb. If the limb is too hot, the thermal elements can cool the limb to inhibit or prevent blistering, excessive perspiration, and/or discomfort.

FIGS. 18-21 show the liner system 610 including an inner layer 620 and a ventilation layer or liner 640. The ventilation layer 640 includes a plurality of ventilation features. The illustrated ventilation layer 640 is a perforated compliant liner with an array of through-holes. Ventilation features can also include, without limitation, open channels, closed channels, wicking materials, reinforcement features, through-holes, and combinations thereof. The inner layer 620 overlays at least a substantial portion of the layer 640 and defines a cavity 632. When the user inserts a limb into the liner system 610, the inner layer 620 is sandwiched between the user's skin and the layer 640.

The inner layer 620 can function as a barrier layer to form a generally air-tight seal with the user's skin to help suspend the prosthesis 600 from the limb. The inner layer 620 can also be permeable or semi-permeable to moisture (e.g., water vapor) to allow moisture to escape from between the user's skin and the inner layer 620. This can help to maintain an air-tight seal while eliminating many problems associated with excess moisture at the skin interface. The inner layer 620 can be a membrane with a monolayer or multilayer construction. In monolayer embodiments, the membrane 620 can directly contact the user's skin. In multilayer embodiments, the membrane 620 may have a contact layer for contacting the user's skin and another layer (or layers) coupled to the contact layer. The contact layer can be made of a fabric or other suitable material for contacting the user's skin.

The layer 640 can have a generally tubular body with a closed end 641. The closed end 641 can be placed in the bottom of the socket 619. The layer 640 can provide cushioning to help provide comfort to the user. Rubber, elastomers, polymers, plastics, foam (e.g., open cell foam, closed cell foam, or the like), or other compliant or semi-compliant materials can form the layer 640. To promote fluid flow across the thickness of the layer 640, the layer 640 can comprise a wicking material.

The liner system 610 can be manufactured by forming the layer 640. A body 643 of the layer 640 can be formed via an extrusion process, molding process (e.g., an injection molding process, a compression molding process, or other suitable process), dipping, or the like. The body 643 can be made of an extrudable or moldable material, such as rubber, silicone, urethane, or mineral oil gel. If the body 643 is formed via a molding process, through-holes can be formed during molding. If the body 643 is extruded, the through-holes can be formed after the extrusion process by a punching process, drilling process, or other suitable hole-forming process.

The inner layer 620 is coupled to the ventilation layer 640 by rolling the layer 640 inside out and coating it with a thin layer of adhesive. The inner layer 620 is then affixed to the layer 640. In other processes, the inner layer 620 is formed by spraying, coating, dipping, or otherwise depositing material onto the layer 640 with or without turning the layer 640 inside out. For example, the inner layer 620 can be cured to the layer 640. The processed use to couple the inner layer 620 to the layer 640 can be selected based on the configuration of the layer 640 and the properties of the inner layer 620.

Referring again to FIGS. 18-21, the inner layer 620 overlays an inner surface 650 of the layer 640. Through-holes 649 (see FIG. 21) extend between the inner surface 650 and an outer surface 651. The inner layer 620 covers the though-holes 649 such that moisture passes through the inner layer 620 and through the through-holes 649.

The layer 640 has generally evenly spaced-apart through-holes 649.

The size, position, pattern, and spacing of the through-holes can be selected based on the desired moisture removal capabilities of the liner system 600. For example, the number of through-holes can be increased to increase the rate at which moisture is removed from the cavity 632.

Figure 25:
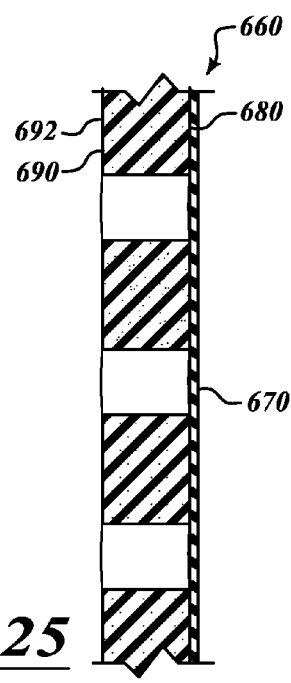
FIG. 25 is a detailed view of a portion of the liner system of FIG. 24.

FIGS. 22-25 show a liner system 660 that includes an outer layer 670 (e.g., a barrier layer) overlaying an outer surface 680 of a ventilation layer 690. Through-holes extend between an inner surface 692 and an outer surface 680 of the ventilation layer 690, as shown in FIG. 25. The outer layer 670 covers the though-holes such that moisture passes through the through-holes and then the outer layer 670. When the liner system 660 is installed in a socket, the outer layer 670 is between the layer 690 and an inner surface of the socket.

FIGS. 26-28 show a liner system 700 that includes a ventilation layer or liner 702 and an inner layer 704. The inner layer 704 overlies a plurality of circumferentially spaced-apart channels extending along the interior region of the liner 702. Moisture that has passed through the inner layer 704 can travel readily along these channels and ultimately out of the liner system 700.

Channels can extend longitudinally (shown in FIG. 28), circumferentially, diagonally, or in any other orientation. The channels can have generally U-shaped cross-sections, V-shaped cross-sections, or any other cross-section suitable for defining a fluid pathway. The channels can be interconnected to form a network to facilitate distribution of fluid (e.g., moisture vapor, sweat, or the like) along the liner system 700.

Figure 29:
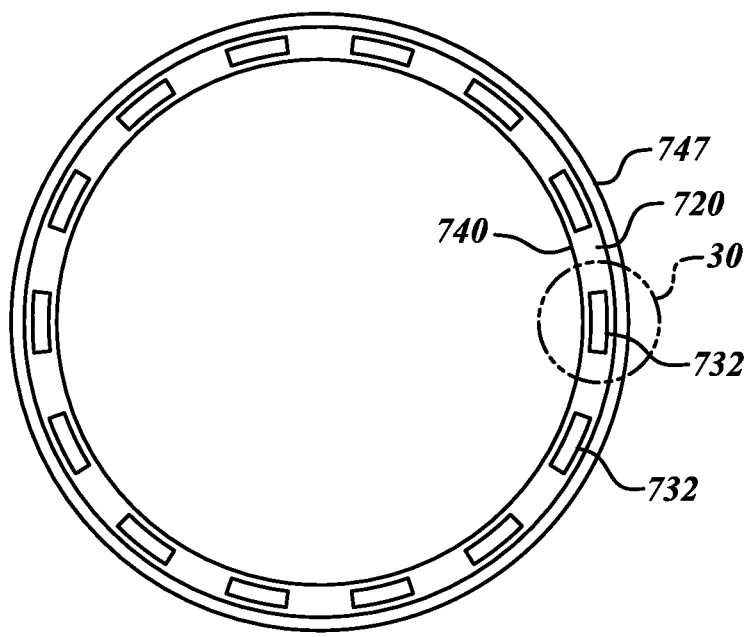
FIG. 29 is a plan view of a liner system having a plurality of embedded channels.
Figure 30:
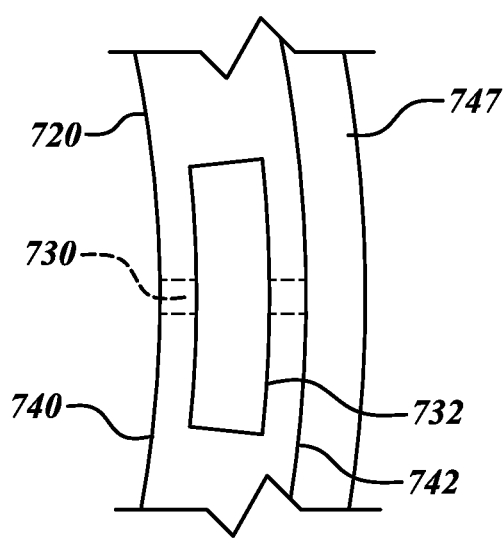
FIG. 30 is a detailed view of a portion of the liner system of FIG. 29.

FIGS. 29-30 show different channel arrangements. FIG. 30 shows channels that extend through a ventilation layer or liner 720. Through-holes 730 (illustrated in dashed line) provide fluid communication across the thickness of the liner 720 while fluid channels 732 provide fluid flow along the length of the liner 720. The illustrated through-hole 730 of FIG. 30 fluidically couples the embedded channel 732 to surfaces 740, 742. The through-hole 730 also provides fluid communication to an outer layer in the form of a membrane 747.

Figure 31:
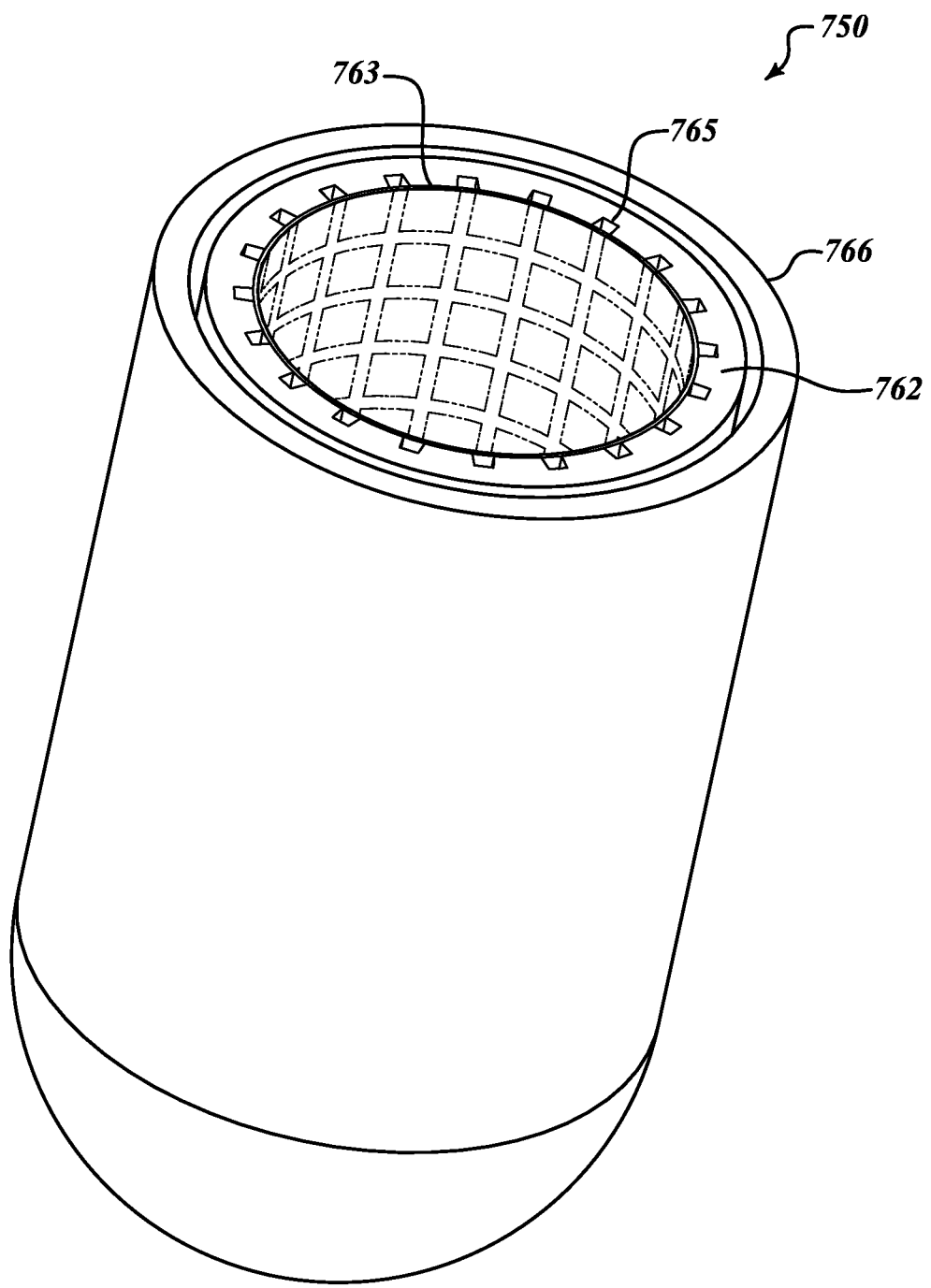
FIG. 31 is a perspective view of a liner system with a network of channels.

FIG. 31 shows a liner system 750 comprising a liner 762, an inner layer 763 (e.g., a barrier layer in the form of a membrane), and channels 765. The liner 762 is between the membrane 763 and a socket main body 766. The channels 765 form a network. The illustrated network of channels 765 (illustrated in dashed line) includes a first set of spaced apart circumferentially extending channels and a second set of spaced apart longitudinally extending channels.

The liner system 750 is formed by forming the channels 765 in the liner 762. This can be accomplished by either removing material from the liner 762, or through the use of a positive mold. The membrane 763 can be coupled to the liner 762 by rolling the liner inside out and coating it with a thin layer of adhesive. The membrane 763 is then attached to the liner 762.

Figure 32:
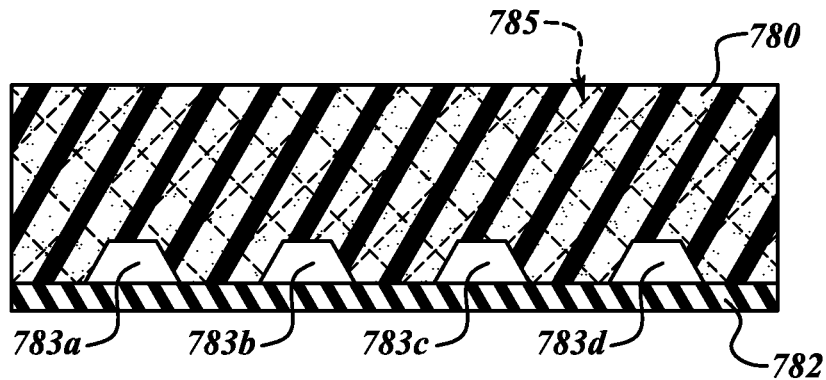
FIG. 32 is a cross-sectional view of a portion of a liner system including a ventilation layer with channels and a barrier layer.

FIG. 32 shows a section of a liner system. The liner system includes a ventilation layer or liner 780 and a membrane 782. Channels 783*a*-783*d* (collectively "783") are formed in the liner 780. The membrane 782 can be affixed or otherwise coupled to the liner 780 and extends across each of the channels 783.

The liner 780 can have one or more reinforcement features 785 to adjust the mechanical properties of the liner system 750 to prevent deformation (e.g., collapsing) of the channels 783. In certain embodiments, the reinforcement features 785 (illustrated in dashed line) are embedded rigid fibers or filaments or other embodiments. The reinforcement features can be structures that increase the structural strength of the material forming the liner 780, thereby substantially eliminating, inhibiting, or limiting collapse of the channels 783. The reinforcement features 785 can be made of a material that can withstand forces in tension and/or compression, but can deform in bending or torsion. For example, the reinforcement features can be made, in whole or in part, of metal, polymers, or rigid fibrous materials.

Figure 33:
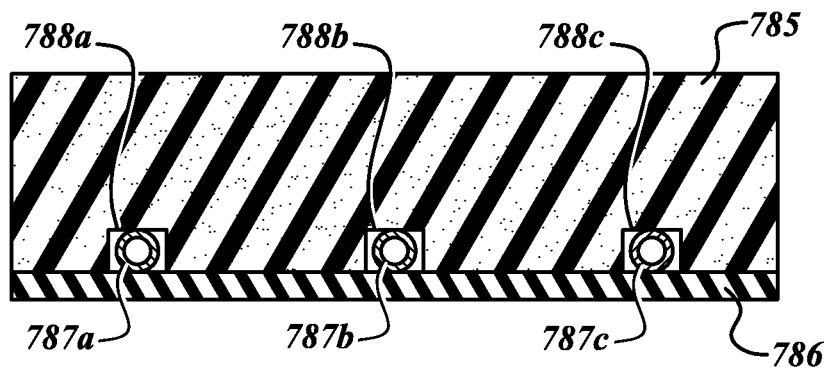
FIG. 33 is a cross-sectional view of a portion of a liner system with intralumenal reinforcement features.

FIG. 33 shows a portion of the liner system including a ventilation layer or liner 785 and a membrane 786. A plurality of reinforcement structures 787*a*-787*c* (collectively "787") are positioned in lumens of channels 788*a*-788*c* (collectively "788") to prevent excessive deformation of the channels 788. The structures 787 can be generally rigid hollow members (e.g., scaffolds, metal tubes, rigid polymer tubes, or any other structures through which fluid can flow while shaping the channels 788). The reinforcement structures 787 can be sufficiently rigid to maintain their shape under a load and can also be hollow, and/or perforated to allow the passage of air, water, or the like.

Figure 34:
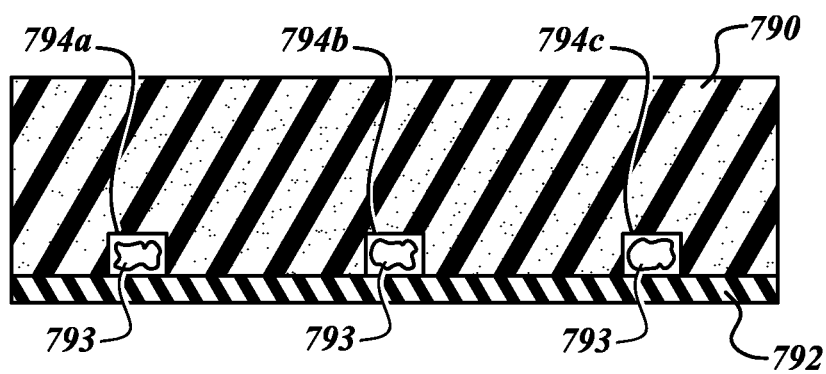
FIG. 34 is a cross-sectional view of a liner system with a wicking material in channels.

FIG. 34 shows a liner system including a ventilation layer or liner 790, a membrane 792, and moisture transfer material 793. The moisture transfer material 793 can promote fluid movement through channels 794*a*-794*c* (collectively "794"). In the illustrated embodiment, the moisture transfer material 793 is located within the lumens of the channels 794*a*-794*c* and promotes movement of liquid. In certain embodiments, the material 793 helps distribute the liquid, if any, throughout the liner system. Of course, the liner 790 can have through-holes or any other features to help ventilation. The moisture transfer material 793 can also help keep the channels 794 open, especially when significant pressure is applied to the liner system. A wide range of wicking materials (e.g., polypropylene, sheep's wool, etc.) or other types of similar material can be used to form the moisture transfer material 793.

The liner systems of FIGS. 32-34 can be incorporated into the prostheses disclosed herein. The ventilation capabilities of the liner system can be selected based on the design of the prosthesis. For example, the liner system of FIG. 32 can line the socket main body 124 of FIG. 1 because appreciable loads may be applied to the liner system. The liner system of FIG. 33 can line the panel 120 because the panel 120 may not be subjected to significant loads. Of course, different types of ventilation features can be mixed and matched to enhance functionality. For example, wicking or fluid transfer materials can be used in combination with the rigid reinforcement structures 787 (see FIG. 33) to achieve the desired mechanical properties and ventilation characteristics.

Figure 35:
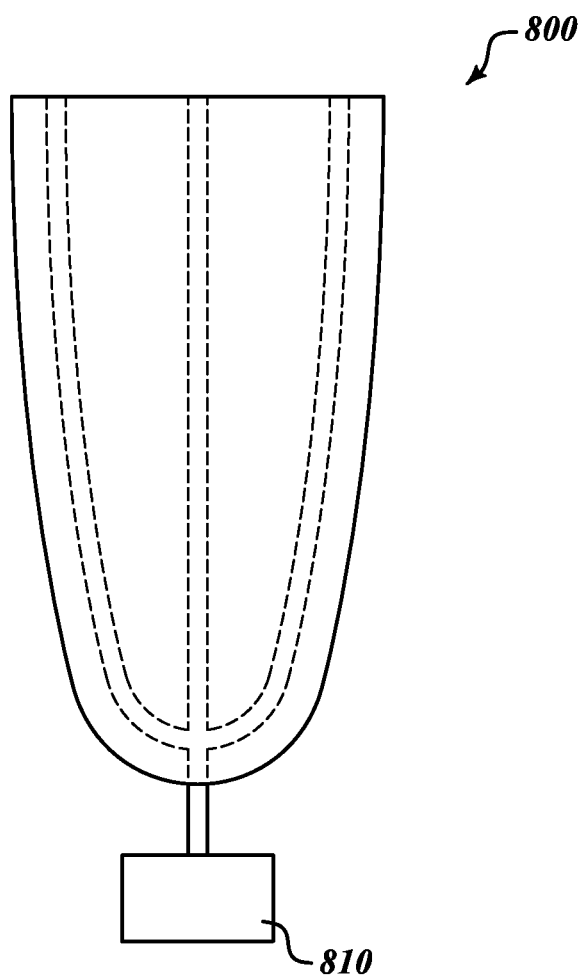
FIG. 35 is an elevational view of a socket with a pressurization device.

FIG. 35 shows a pressurization device 810 that causes fluid flow through a liner system 800. The pressurization device 810 can be coupled to a socket main body, a panel, a pylon, or any other component of the prosthesis, or coupled (e.g., strapped) to the user. The pressurization device 810 can cause fluid flow through ventilation features to control humidity, the amount of water vapor at interfaces, temperatures, properties of the liner system 800 (e.g., compressibility), or the like. In some embodiments, the pressurization device 810 comprises a fan that forces air into channels (shown in dashed line) via a pin lock or fluid line to help remove moisture from the liner system 800. In other embodiments, the pressurization device 810 is a pump that draws air through the channels.

The pressurization device 810 can also be used to draw a negative pressure between the user's body and the socket. Such embodiments are well suited for performing negative pressure therapy to facilitate healing. In some embodiments, a prosthesis includes a plurality of pressurization devices that can independently provide a vacuum between the user and the socket, and to cause an airflow or ventilation via a liner system.

Unless the context requires otherwise, throughout the specification and claims which follow, the word "comprise" and variations thereof, such as, "comprises" and "comprising" are to be construed in an open, inclusive sense, that is as "including, but not limited to."

As used in this specification and the claims, the singular forms "a," "an," and "the" include plural referents unless the content clearly dictates otherwise. It should also be noted that the term "or" is generally employed in its sense including "and/or" unless the context clearly dictates otherwise.

The various embodiments described above can be combined to provide further embodiments. The couplers, mandrels, fasteners and other components and features disclosed herein can be mixed and matched based on the desired installation. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A prosthesis, comprising:
   a liner system for placement in a socket, the liner system including:
      a water vapor permeable, air barrier layer having a front side and a back side, the front side defining an interior cavity, wherein the water vapor permeable, air barrier layer is capable of maintaining a vacuum with a residual limb positioned in the interior cavity;
      a ventilation layer on the back side of the barrier layer, the ventilation layer including a plurality of venting features through which moisture passes to manage moisture at an interface between the user's skin and the liner system, the venting features including channels; and
      at least one reinforcement structure positioned along the channels and configured to keep the channels open, wherein the at least one reinforcement structure includes a plurality of tubular members positioned within lumens of the channels.

2. The prosthesis of claim 1, wherein the venting features further include a plurality of spaced apart through-holes extending between opposing sides of the ventilation layer.

3. The prosthesis of claim 1, wherein the barrier layer extends across the channels to define passages.

4. The prosthesis of claim 1, further comprising:
   a pressurization device in fluid communication with the venting features to cause fluid flow through the venting features.

5. The prosthesis of claim 4, wherein the pressurization device is a fan to push fluid through the ventilation features or a pump to draw fluid through the ventilation features.

6. The prosthesis of claim 1, further comprising a wicking material within the channels, wherein the wicking material is positioned to transport moisture that passes across the barrier layer through the channels.

7. The prosthesis of claim 1, wherein the barrier layer overlays the plurality of venting features.

8. The prosthesis of claim 1, further comprising:
   a pressurization device;
   a socket lined by the liner system; and
   a plurality of sensors positioned at different locations along the socket, the sensors are in communication with the pressurization device such that the pressurization device operates in response to one or more signals from the sensors.

9. The prosthesis of claim 1, wherein the channels are circumferentially spaced apart from one another when the liner system is positioned in a socket and covered by the water vapor permeable, air barrier layer.

10. The prosthesis of claim 9, wherein the channels extend along at least most of a longitudinal length of the socket.

11. The prosthesis of claim 1, wherein the water vapor permeable, air barrier layer is substantially impermeable to air flow therethrough such that an airtight seal is capable of being formed with a residual limb positioned in the interior cavity.

12. The prosthesis of claim 11, wherein the water vapor permeable, air barrier layer comprises a polyestherester membrane.

13. The prosthesis of claim 11, wherein the water vapor permeable, air barrier layer overlays most of the ventilation layer and is substantially impermeable to air flow therethrough.

14. The prosthesis of claim 1, wherein the water vapor permeable, air barrier layer comprises a hydrophobic material and a hydrophilic material.

15. The prosthesis of claim 1, wherein the water vapor permeable, air barrier layer comprises a layer of tightly-woven fibers, portions of the fibers are hydrophobic and portions of the fibers are hydrophilic.

16. The prosthesis of claim 1, wherein the water vapor permeable, air barrier layer includes a membrane that overlays most of the ventilation layer, the membrane is configured to form an air-tight seal with a user's skin.

17. The prosthesis of claim 1, wherein the water vapor permeable, air barrier layer is a monolayer membrane.

18. The prosthesis of claim 1, further comprising a socket, wherein the liner system is positioned in the socket.

19. The prosthesis of claim 1, wherein the water vapor permeable, air barrier layer includes a hydrophilic portion and a hydrophobic portion, the hydrophilic portion is positioned to contact and draw water vapor in the interior cavity through the hydrophilic portion and into contact with the hydrophobic portion, the hydrophobic portion is configured to move the water vapor out the backside of the water vapor permeable, air barrier layer.

20. A prosthesis, comprising:
   a liner system for placement in a socket, the liner system including:
      a water vapor permeable, air barrier layer having a front side and a back side, the front side defining at least most of an interior cavity such that an air tight seal is capable of being formed with a residual limb positioned in the interior cavity to maintain a vacuum between the residual limb and the water vapor permeable, air barrier layer; and
      a ventilation layer positioned on the back side of the water vapor permeable, air barrier layer and including a plurality of venting features, wherein the water vapor permeable, air barrier layer overlays most of the ventilation layer such that the venting features receive moisture exiting the back side of the water vapor permeable, air barrier layer, wherein the venting features include channels; and
      a plurality of hollow reinforcement structures positioned in the channels, wherein the hollow reinforcement structures are positioned to prevent collapse of the channels, and wherein the hollow reinforcement structures are substantially parallel to the front side of the water vapor permeable, air barrier layer.

21. The prosthesis of claim 20, wherein the water vapor permeable, air barrier layer is configured to allow water vapor to pass therethrough while an air tight seal is maintained with the residual limb positioned in the interior cavity.

22. The prosthesis of claim 20, wherein the water vapor permeable, air barrier layer includes a hydrophilic portion and a hydrophobic portion, the hydrophilic portion is positioned to contact and draw water vapor from the interior cavity towards the hydrophobic portion, the hydrophobic portion is configured to move the water vapor out the back side of the water vapor permeable, air barrier layer.

23. The prosthesis of claim 20, wherein the water vapor permeable, air barrier layer is a monolayer membrane.

24. The prosthesis of claim 20, further comprising a socket, wherein the liner system is positioned in the socket.

* * * * *